US009352065B2

(12) United States Patent
Habbel

(10) Patent No.: US 9,352,065 B2
(45) Date of Patent: May 31, 2016

(54) SCENT DISPERSER ARRANGEMENT IN AN HVAC SYSTEM

(71) Applicant: Sam Habbel, Scottsdale, AZ (US)

(72) Inventor: Sam Habbel, Scottsdale, AZ (US)

( * ) Notice: Subject to any disclaimer, the term of this patent is extended or adjusted under 35 U.S.C. 154(b) by 854 days.

(21) Appl. No.: 13/573,813

(22) Filed: Oct. 5, 2012

(65) Prior Publication Data

US 2014/0097266 A1   Apr. 10, 2014

(51) Int. Cl.
*F24F 6/00* (2006.01)
*F24F 7/00* (2006.01)
*A61L 9/14* (2006.01)
*B65D 83/26* (2006.01)
*B65D 83/30* (2006.01)
*B65D 83/38* (2006.01)
*B65D 83/62* (2006.01)
*B65D 83/68* (2006.01)
*A61L 2/00* (2006.01)
*A61L 9/00* (2006.01)
*B65D 83/14* (2006.01)
*F24F 3/16* (2006.01)
*F24F 11/00* (2006.01)

(52) U.S. Cl.
CPC ... *A61L 9/14* (2013.01); *A61L 2/00* (2013.01); *A61L 9/00* (2013.01); *B65D 83/262* (2013.01); *B65D 83/265* (2013.01); *B65D 83/303* (2013.01); *B65D 83/384* (2013.01); *B65D 83/388* (2013.01); *B65D 83/62* (2013.01); *B65D 83/682* (2013.01); *A61L 2209/111* (2013.01); *A61L 2209/16* (2013.01); *B65D 83/759* (2013.01); *F24F 2003/1689* (2013.01); *F24F 2011/0038* (2013.01)

(58) Field of Classification Search
CPC .................. F24F 2003/1689; A61L 7/1499
USPC .......................................... 454/337
See application file for complete search history.

(56) References Cited

U.S. PATENT DOCUMENTS

| 4,903,583 | A | * | 2/1990 | Frazier ................. 454/337 |
| 5,301,873 | A |  | 4/1994 | Burke et al. |
| 5,533,705 | A |  | 7/1996 | Zlotnik |
| 5,816,846 | A |  | 10/1998 | Zlotnik |
| 5,924,597 | A | * | 7/1999 | Lynn ..................... 222/1 |
| 6,105,916 | A |  | 8/2000 | Zlotnik |
| 6,161,725 | A | * | 12/2000 | Dean .................... 222/23 |
| 6,347,992 | B1 | * | 2/2002 | Durbin et al. .......... 454/337 |
| 6,379,242 | B1 | * | 4/2002 | Wiseman et al. ....... 454/337 |

(Continued)

*Primary Examiner* — Steven B McAllister
*Assistant Examiner* — Jonathan Cotov
(74) *Attorney, Agent, or Firm* — Paul Bogdon

(57) ABSTRACT

Scent dispenser arrangement for dispersing fragrance into a HVAC system includes a flow sensor and a scent disperser assembly having a control module connected to the flow sensor and a canister for emitting a spray which is actuated by the control module. The flow sensor operates in response to air flow and creates an air flow dependent electrical signal transmitted to activate the control module of the spray disperser assembly. The scent disperser and flow sensor are arranged to allow the spray to be disbursed in selective locations in the HVAC system. An embodiment involves two scent disperser assemblies electrically connected in series which operate successively when the liquid in one dispenser assembly is depleted or when one dispenser assembly dispersers a predetermined number of sprays. A further embodiment involves pressurized containers which communicate with a scented liquid reservoir having a sprayer, wherein a pressure differential in the reservoir triggers the pressurized containers to deliver a liquid flow into the reservoir.

17 Claims, 24 Drawing Sheets

(56) References Cited

U.S. PATENT DOCUMENTS

| | | | |
|---|---|---|---|
| 6,435,419 B1 * | 8/2002 | Davis | 237/78 R |
| 6,553,777 B2 * | 4/2003 | Dillenback | 62/171 |
| 6,722,529 B2 * | 4/2004 | Ceppaluni et al. | 222/63 |
| 6,766,651 B2 * | 7/2004 | Dillenback | 62/180 |
| 6,957,779 B2 | 10/2005 | Joshi | |
| 7,135,169 B2 * | 11/2006 | Maleeny et al. | 424/76.1 |
| 7,543,761 B2 * | 6/2009 | Mehus et al. | 239/10 |
| 7,547,364 B2 * | 6/2009 | Polak | 134/26 |
| 2003/0230091 A1 * | 12/2003 | Dillenback | 62/91 |
| 2006/0121844 A1 * | 6/2006 | Sparks | 454/337 |
| 2007/0181000 A1 * | 8/2007 | Wilson et al. | 96/134 |
| 2008/0243273 A1 * | 10/2008 | Robert et al. | 700/67 |
| 2010/0070086 A1 * | 3/2010 | Harrod et al. | 700/276 |

* cited by examiner

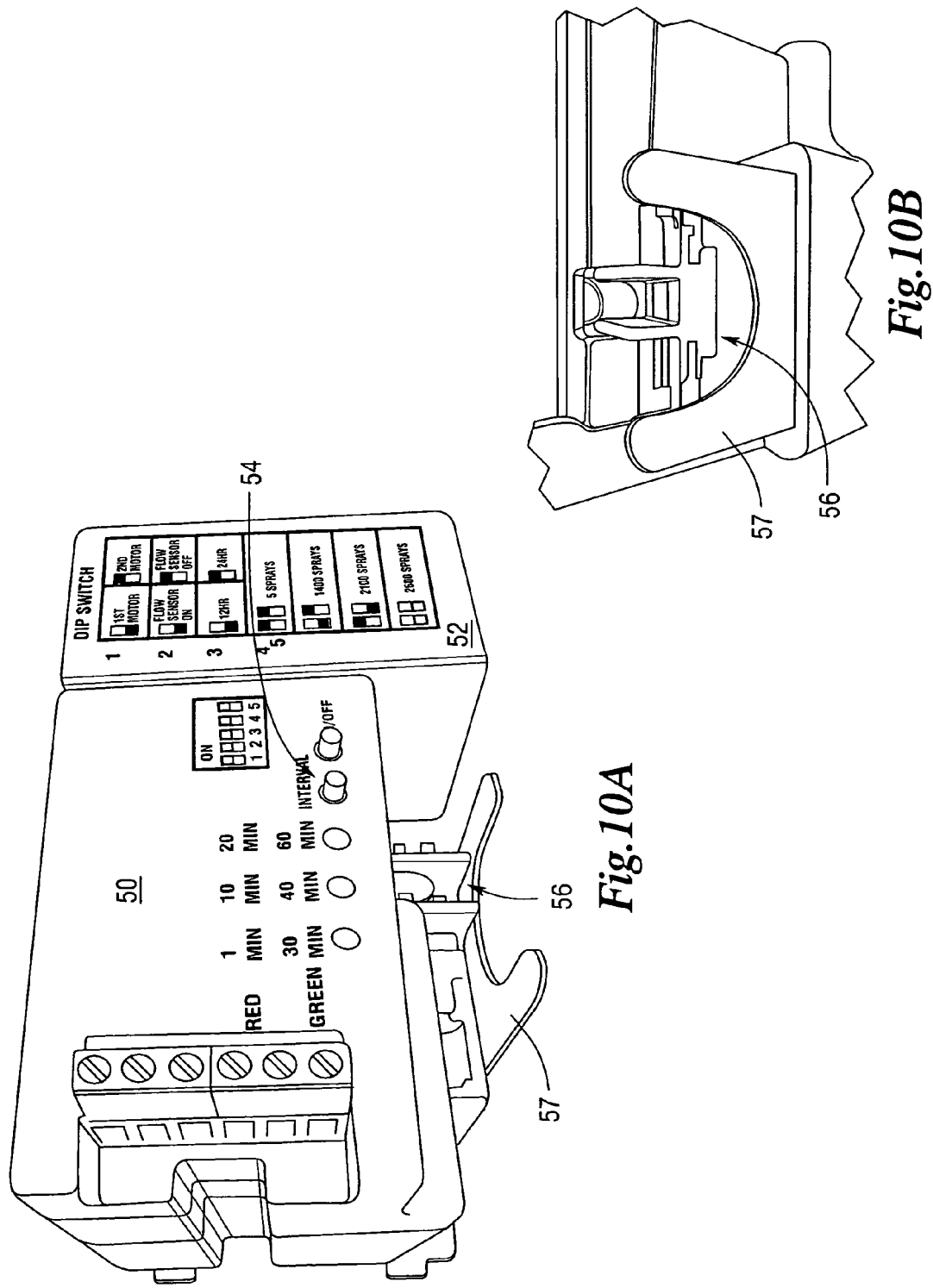

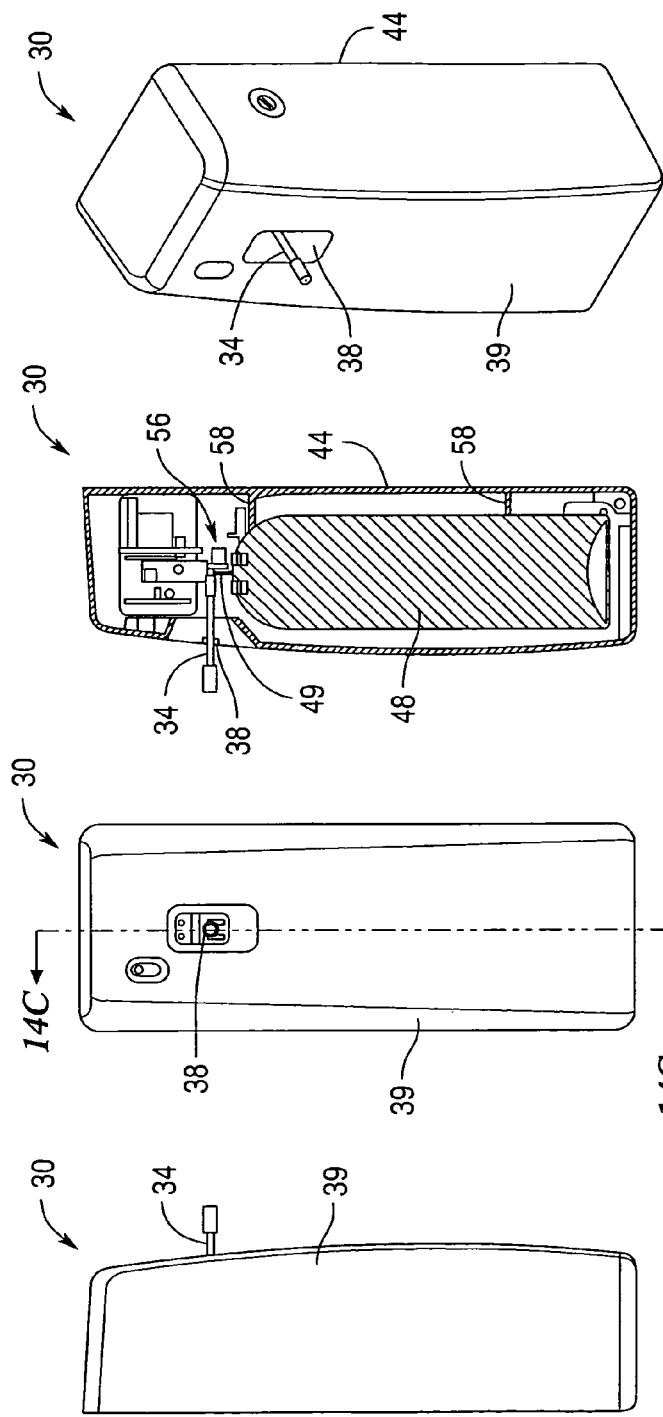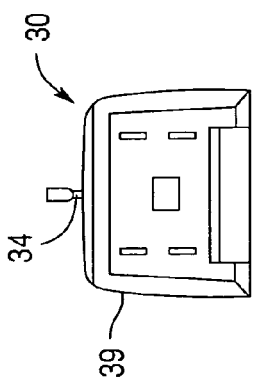

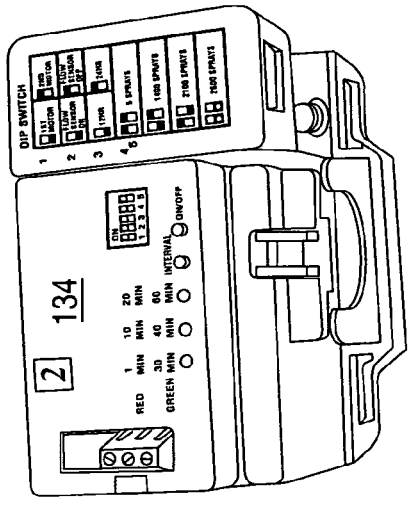
Now, not identical
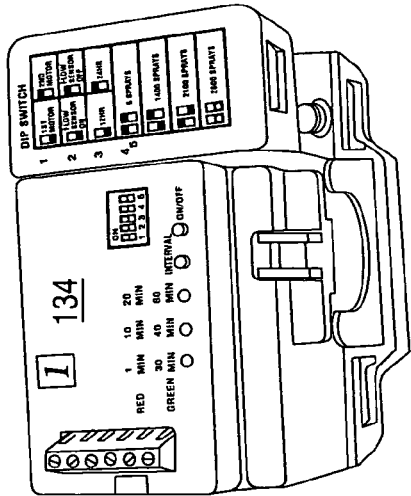
To be identical and switchable between primary and secondary
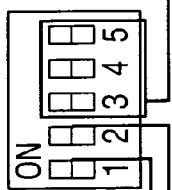
*Plan 1*
Primary/Secondary
Flow Sensor ON/Off
| | 5 | 1400 | 2100 | 2600 |
|---|---|---|---|---|
| Any of the 9 combination | | | | |
| Link ON/OFF | | | | |
| 12 Hr/24Hr | | | | |
*Plan 2* Same as Plan 1 Except there are 2 dip switch
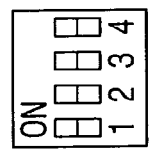
Everything else
*Fig.22*

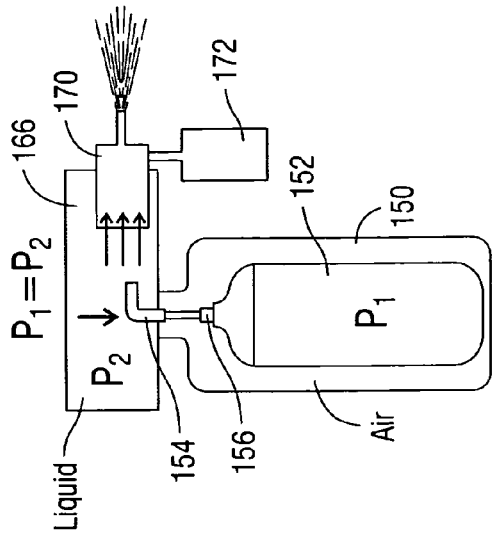
Fig.24
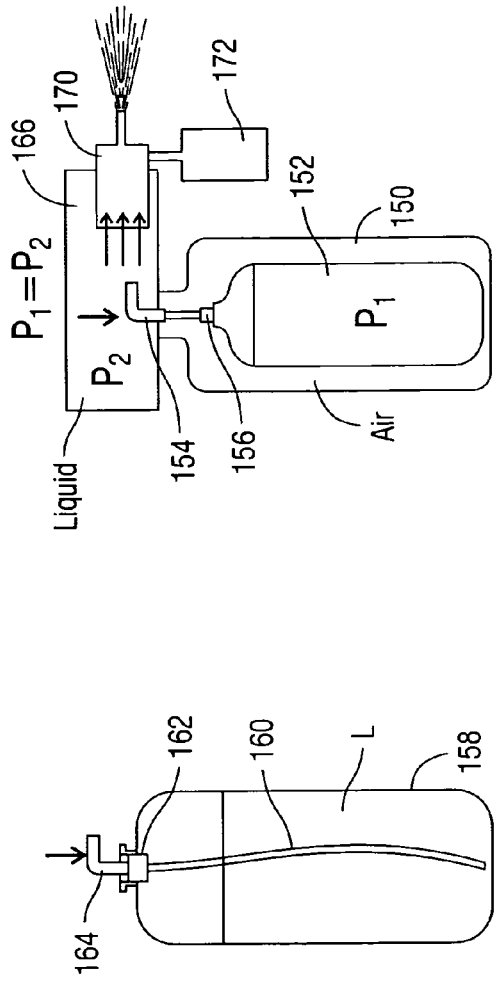
Fig.25
Fig.26
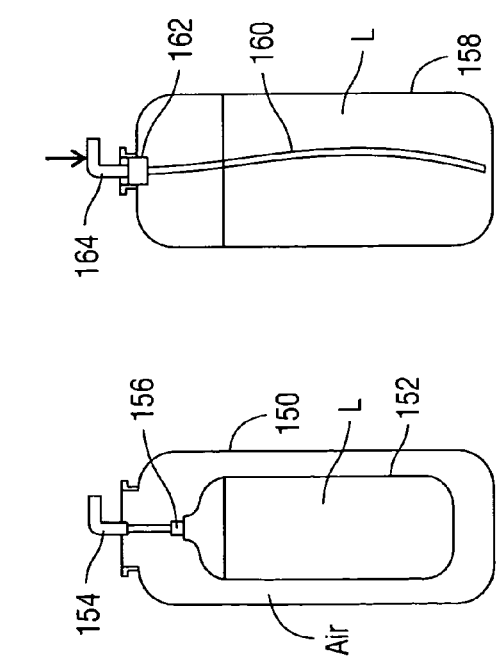
Fig.27

SCENT DISPERSER ARRANGEMENT IN AN HVAC SYSTEM

This application claims priority to U.S. Provisional Patent Application Ser. No. 61/626,996, filed Oct. 6, 2011, the disclosure of which is incorporated by reference in its entirety.

BACKGROUND OF THE INVENTION

1. Field of the Invention

The invention relates to an HVAC system and a scent disperser arrangement in the HVAC system in residential and commercial establishments. More particularly, the invention relates to a scent disperser arrangement comprising a flow sensor and one or more scent disperser assemblies; a computer program for operating the scent disperser assemblies; a pressurized reservoir containing one or more pressurized liquid scent canisters wherein a pressure differential in the reservoir triggers the flow of liquid from the scent canisters into the reservoir; and a unique design for the canister of the scent disperser assembly.

2. Description of Related Art

Deodorizers are currently used to deodorize commodes and urinals, particularly in the restrooms of institutions and places frequented by the public, although they may also be used in homes. Deodorizer cabinets or frames are generally provided for such deodorizers. Examples of such cabinets or frames are disclosed in U.S. Pat. Nos. 5,533,705; 5,816,846; and 6,105,916. These dispensers provide a drive selectively using a large or small motor providing an air stream for generating vapor from a wick, ceramic wafers, or discs containing vaporizable deodorant and reversible drive mounting mounted back-to-back. U.S. Pat. No. 6,957,779 discloses a framed fluid delivery device that includes a fluid delivery cartridge for the timed-release delivery of a fluid. These known deodorant dispensers are commonly used and recognized by the public because of their use for dispersing fragrances in hostile environments, such as restrooms where it is desirous to control the nature of the atmosphere.

Building dwellers are concerned with the quality of the ambient indoor air. Offensive orders affect the quality of indoor air, and the art has provided several systems for masking these odors.

U.S. Pat. No. 5,924,597 pertains generally to the field of fragrance distribution inside buildings and pertains specifically to dispensing selected types and quantities of fragrances into the existing heating-ventilation-air condition (HVAC) ductwork that supplies air to different rooms within the building. This '597 patent discloses a fragrance dispensing apparatus and a method for use of the apparatus in a multi-room building having an existing HVAC system ventilated by a forcing fan. The apparatus includes fragrance containers, several solenoids, programmable timers and a single fan timer. The fragrance container is mounted in communication with the HVAC ductwork leading into a given room and is controlled by a separate solenoid, which is in turn, controlled by a separate programmable timer. All of the programmable timers are connected to the single fan timer which controls the operation of the forcing fan. The method allows one or more of the programmable timers to activate corresponding containers to dispense fragrances as the forcing fan runs to distribute the fragrances into the rooms supplied by the ductwork.

U.S. Pat. No. 4,903,583 discloses an aerosol air and ductwork treatment apparatus for HVAC systems. The apparatus includes a housing which is received on the exterior of a central air conditioning ductwork communicating with the interior of the ductwork downstream of the existing return air filter and fan system for discharging air treatment chemicals into the air flowing through the ductwork, and is connected to the existing electrical circuitry with an adjustable timer and is manually operable by a push button switch to control the operation of an aerosol dispenser for a selective period of time and to run the existing fan system for a selective period of time following the operation of the aerosol dispenser to distribute the air treatment chemicals throughout the ductworks and into the rooms served thereby.

U.S. Pat. No. 6,347,992 discloses a ductwork air freshener apparatus for distributing fresh air evenly throughout the building using the existing air ductworks. The ductwork air freshener apparatus includes a housing assembly designed to be mounted to the ductwork of the house. A pressurized air freshener container is removably inserted into the housing assembly. An actuation assembly actuates the pressurized air freshener container whereby the deodorizing fragrance is designed for introduction into the ductwork. The actuation assembly is coupled to the housing assembly. A control assembly is coupled to the housing and is operationally coupled to the actuation assembly whereby the control assembly actuates the actuation assembly upon the control assembly satisfying a predetermined condition. As disclosed in column 5, lines 32 to 35, a predetermined condition is a drop in pressure around the sensor switch when the air flow in the ductwork is moving past the sensor switch. The sensor switch is part of the control assembly and is operationally coupled to the actuation assembly whereby the sensor switch actuates the actuation assembly when the sensor switch detects the predetermined condition.

U.S. Pat. No. 7,135,169 discloses an air scenting device for use in mechanical HVAC systems wherein air is circulated within an interior space. An HVAC housing has an ambient air inlet end and an outlet end connected to an air outlet ducting which disperses filtered air into the surrounding environment. Mounted in the housing is a filter and a fan or blower assembly for controlling the ambient air flow through the housing in the direction indicated by arrows a and b from the inlet end of the housing through the filter from the filter's upstream facing surface to its downstream facing surface and then to outlet end of the housing and into the air outlet ducting for distribution into the surrounding environment. An aqueous scenting composition is applied in spray form directly onto the filter medium from a suitable spray application device which may be a simple button operated spray jar or may be a more technically advanced pump arrangement having a head assembly with interchangeable orifice caps to provide nozzles of varying dimensions for accurate adjustment of the spray droplet size in the spray sprayed onto the surface of the filter medium of the air filters.

U.S. Pat. No. 6,722,529 discloses a housing mounted to the ductwork of a hot air heating system or a central air conditioning system and includes a pressure differential switch having a sensing tube to sense the forced air flow in actuating a spray dispenser to discharge a freshening, deodorizing and/ or disinfecting spray through a nozzle. In securing the dispenser in position between clips, its orientation is such that the discharge nozzle of the dispenser extends rearward towards the aperture of housing to join with a hose coupling the nozzle through the housing and into the ductwork. The hose sprays a misted product into the ductwork.

U.S. Pat. No. 6,347,992 relates to a ductwork air freshener apparatus for distributing fresh air evenly throughout the building using the existing air ductworks. The ductwork air freshener apparatus includes a housing assembly designed for mounting to the ductwork of the house. A pressurized air freshener container is removably inserted into the housing assembly. An actuation assembly is for actuating the pressurized air freshener container whereby the deodorizing fragrance is designed for introduction into the ductwork of the house. The actuation assembly is coupled to the housing assembly. A control assembly is coupled to the housing and is operationally coupled to the actuation assembly whereby the control assembly actuates the actuation assembly upon the control assembly satisfying a predetermined condition. As disclosed in column 5, lines 32 to 35, a predetermined condition is a drop in pressure around the sensor switch when the air flow in the ductwork is moving past the sensor switch. The sensor switch is part of the control assembly and is operationally coupled to the actuation assembly whereby the sensor switch actuates the actuation assembly when the sensor switch detects the predetermined condition.

U.S. Pat. No. 5,301,873 discloses a low fluid indicator for a fluid injection system of the type having a sealed pressurized canister, and a valve responsive to a control signal to release fluid from the canister. If the system is intended to disinfect or deodorize a space serviced by a forced air HVAC system, the fluid in the canister can be suitable deodorant or disinfectant.

U.S. Patent Application No. 2003/0230091 discloses a user-programmable monitoring and dispensing system for controlling the dispensing of water vapor and various other media into an HVAC air stream in residential or commercial structures. These materials may be fragrances or aromas, intended to produce an aesthetic effect, or they can be agents capable of pesticidal, bacteriacidal, fungicidal or sporacidal effect for use as acute treatment for infestation as disclosed in the abstract. As disclosed in paragraph [0023] the HVAC system illustrated includes an air movement generating device, such as a blower which generates an air stream which pass through ductwork work to a desired residential or commercial space. Positioned downstream from the blower, heat exchanger and A/C coil, in the direction of air movement, is a pressure or flow sensor . . . a humidity sensor and a temperature sensor . . . , all of which are connected to a system central processor . . . for providing air stream sensor inputs as to the air movement, moisture content of the air stream and the air stream temperature to the system central processor . . . . However, it is to be understood that separate dispensers may be utilized in various truck ductworks as well as the central plenum for dispersal of the medium into specific locations serviced by the HVAC system.

None of the known scent dispenser/dispenser systems provide a desirable combination of element for detecting airflow through the HVAC ducting to thereby effect control of the scent spray. The known systems are essentially on-off systems controlled by way of timers or computer programs where a stoppage of air flow through the HVAC ducting would not cause the scent spray to cease or to resume when the air flow resumes. Also, the known systems are not designed to allow their component to be selectively located at different locations of the HVAC ducting. There is a need to provide improved scent dispenser assemblies arrangements in an HVAC system which would be responsive to air flow or stoppage of air flow.

SUMMARY OF THE INVENTION

This invention has met these needs. An aspect of the invention is to provide a scent disperser arrangement including a scent disperser assembly for dispersing a fragrance into an HVAC system, and which scent disperser assembly is constructed such that: 1) it can be mounted on an external surface of the ductwork of the HVAC system and remote from the blower; or 2) it can be mounted on an external surface of the ductwork of the HVAC system and adjacent to the blower; or 3) it can be mounted on an internal surface of the ducting of the HVAC system and adjacent to the blower; or 4) it can be floor mounted externally of the HVAC system and adjacent to the air filter of the HVAC system. This versatility of different locations for the scent disperser assembly throughout the HVAC system is possible in view of the construction of the housing of the scent disperser assembly wherein an aperture is provided in the back plate so that an elongated tube for delivering the scented liquid spray can project therefrom or the front cover of the housing contains an aperture so that the elongated tube for delivering the scented liquid spray can extend therefrom.

A further aspect of the invention is to provide a scent disperser arrangement for dispersing a fragrance into an HVAC system comprising a scent disperser assembly and a flow sensor electrically connected to the scent disperser assembly and which flow sensor comprises preferably an anemometer comprising a plurality of rotatable cup elements for catching and detecting the air flows in the HVAC system for operation of the scent disperser assembly, and which flow sensor is constructed and arranged to be mounted inside the air ductwork of an HVAC system regardless of the mounting and location of the scent disperser assembly relative to the HVAC system. The scent disperser assembly includes a canister of liquid fragrance scent having an actuator for delivering the scented spray and a control module containing a motor and a plunger assembly which engages the actuator of the canister.

A still further aspect of the invention is to provide a scent disperser arrangement for dispersing a fragrance into an HVAC system comprising a flow sensor; a spray system including a liquid scented canister and an actuator for dispersing the scented spray; and an electronic control module electronically connected to the flow sensor and the spray system for receiving an electrical signal from the flow sensor and for sending an electrical signal to the spray system for operation of the canister. The flow sensor comprises an anemometer having a plurality of cup elements rotatably mounted on the flow sensor for detecting air flows to cause the cup elements to rotate and to create the electrical signal of the flow sensor transmitted to the electronic module of the scent dispenser assembly. An electrical connection in the form of a voltage signal connects the flow sensor to the electronic control module of the scent disperser assembly. The electronic control module comprises a computer program for selectively operating the canister for dispensing the scented spray.

A still further aspect of the invention is to provide a scent disperser assembly having a back cover, a front cover, and an elongated tube for dispersing the scented spray into a predetermined area in the HVAC system; and wherein the back cover and the front cover each have an aperture for receiving and supporting the elongated tube depending on the location of the scent dispenser assembly in the HVAC system.

In an aspect of the invention, the back cover of the scent dispenser assembly is mounted against an external wall surface of the ductwork of the HVAC system; the flow sensor is mounted inside the ductwork of the HVAC system remote from the air blower; and the elongated tube extends through the aperture of the back cover and into the ductwork for dispersing the scented spray into the HVAC system.

In a further aspect of the invention, the back cover of the scent dispenser assembly is mounted against an external wall surface of the ductwork of the HVAC system; the flow sensor is mounted inside the ductwork of the HVAC system adjacent to the air blower; and the elongated tube extends through the aperture of the back cover and into the ductwork for dispersing the scented spray near the air blower and into the HVAC system.

In a still further aspect of the invention, the back cover of the scent dispenser assembly is mounted against an internal wall surface of the air handler near the air filter; the flow sensor is mounted inside the ductwork of the HVAC system remote from the air blower and the scent dispenser assembly; and the elongated tube extends through the aperture in the front cover and into the air handler for dispersing the scented spray into the air filter and into the HVAC system.

In a still further aspect of the invention, the scent dispenser assembly is mounted on the floor of the HVAC system adjacent to the air filter; the flow sensor is mounted inside the ductwork of the HVAC system adjacent to the air blower; and the elongated tube extends through the aperture in the front cover and into the air filter for dispersing the scented spray into the air filter and into the HVAC system.

A further aspect of the invention comprises a scent disperser arrangement containing a flow sensor and at least two scent disperser assemblies, each having a canister with an actuator and an electronic module with a plunger assembly for operation of the actuator. This arrangement includes a computer program for selectively and subsequently operating the scent disperser assemblies in the HVAC system. Each scent disperser assembly contains features to alert the subsequent scent disperser assembly to be activated when the scented liquid in the scent disperser assembly currently being operated has been depleted or when an predetermined number of sprays is dispersed and the first scent dispense is inactivated. An LED, several push buttons and a toggle panel with toggle switches are provided for manual operation of the module and canister and for connecting the operation of the each canister and module of the two assemblies together for delivering scented sprays into the HVAC system according to a predetermined set up. In this arrangement, the scent disperser assemblies are electrically connected in series and the computer program operates the scent disperser assemblies in a manner that when the first scent disperser assembly runs out of liquid or sprays a predetermined number of sprays, the second scent disperser assembly is operated to disperse a scented spray of a predetermined number of sprays in the programmed arrangement where the first scent disperser sprays a predetermined number of sprays and the spraying is then shifted to the second scent disperser which also sprays a predetermined number of sprays, the spraying being cycled between the first and second scent dispersers.

A still further aspect of the invention provides for a novel design for a canister. This is referred to as a "Valve on the Bag" wherein liquid is contained within a bag which is located in the canister and the bag is surrounded by pressurized air. A valve is connected to the bag and is in turn connected to an actuator which extends out of the canister. The pressurized air around the bag causes the valve to be continuously opened and therefore results in a continuous operation of the actuator such that a continuous spray is emitted.

A further aspect of the invention provides a scent disperser assembly comprising a reservoir for retaining a predetermined amount of scented liquid; a spray mechanism connected to the reservoir for delivering a scented liquid spray into the atmosphere; and a plurality of pressurized containers in communication with the reservoir. When the supply of scented liquid in the reservoir decreases, the containers sequentially deliver liquid into reservoir to restore the desired supply of scented liquid in the reservoir. These containers are "Valve on a Bag" canisters which allow the valve of each canister to continuously remain open and in communication with the reservoir.

A still further aspect of the invention provides a scent dispenser assembly computer operated so that options can be selected. These selections can include the day or days of the week in which the sprays are to be emitted; the number of liquid sprays which are to be dispersed which can be in minute or hourly intervals; and the time of the day these dispersions are to be activated, i.e. only in the am hours, only in the pm hours, or selective hours of the day and/or night.

These and other aspects of the invention will be better appreciated and understood when the following description is read in light of the accompanying drawings.

DESCRIPTION OF THE DRAWINGS

FIG. 10A is a front perspective view of the controller of the control module of FIG. 10.

FIG. 10B is a bottom perspective view of the controller of the control module of FIG. 10.

FIG. 14A is a left side view showing the scent disperser assembly of FIG. 13 in assembled form.

FIG. 14B is a front view of the scent disperser assembly of FIG. 14A.

FIG. 14C is a sectional view taken along lines A-A of FIG. 14B.

FIG. 14D is a right side perspective view of the scent disperser assembly of FIG. 14A.

FIG. 14E is a bottom view of the scent disperser assembly of FIG. 14B.

FIG. 22 are perspective views of the first and second control modules of FIG. 19 and a diagram illustrating the set up for each controller and their use in series.

FIGS. 24 and 25 are schematic illustrations of two different types of canisters that can be used in the scent disperser assembly of the invention.

FIG. 26 is a schematic illustration wherein the canister of FIG. 25A is used.

FIG. 27 is a schematic illustration wherein several canisters are used.

DESCRIPTION OF THE INVENTION

Figure 1:
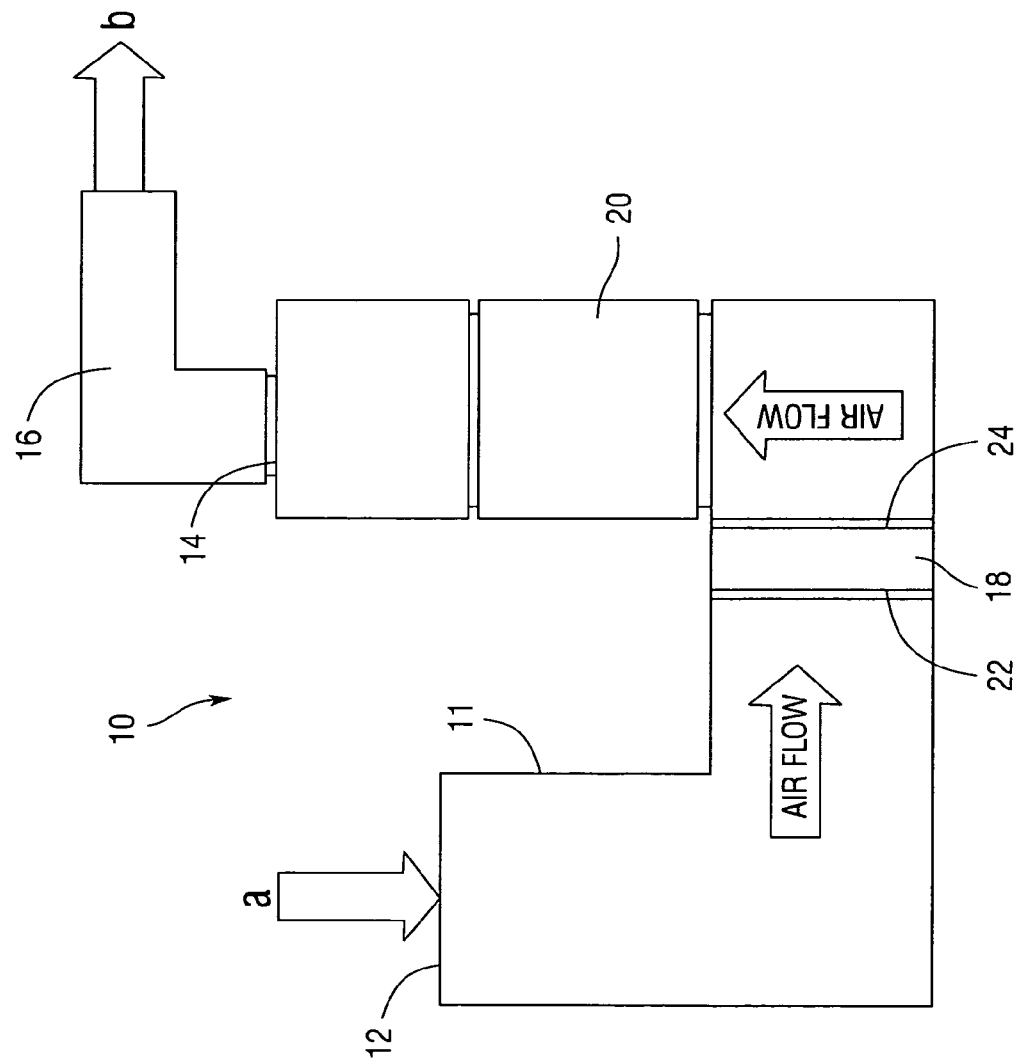
FIG. 1 is a schematic view of a conventional forced air HVAC system.

Referring now to the drawings, FIG. 1 illustrates an example of a conventional forced air heating, ventilating and air condition (HVAC) system 10. HVAC system 10 comprises ductwork 11; an ambient air inlet end 12; and an outlet end 14 connected to an air outlet ductwork 16 which disperses filtered air into the surrounding environment. Mounted in the ductwork 11 is a filter 18 and a fan or blower assembly 20 for controlling the ambient air flow through the ductwork 11 in the direction indicated by arrows a and b from the inlet end 12 of the ductwork 11 through the filter 18 from the filter's upstream facing surface 22 to its downstream facing surface 24 and then to outlet end 14 of the ductwork 11 and into the air outlet ductwork 16 for distribution into the surrounding environment. FIG. 1 exemplifies an HVAC system in which the present invention may be used.

An embodiment of the invention is to provide a scent disperser arrangement which is constructed such that it can be positioned in various locations throughout the ductwork of an HVAC system similar to that of FIG. 1 and still be effective in delivering a scented liquid flow in the ductwork of the HVAC system for distribution into the environment.

Figure 2:
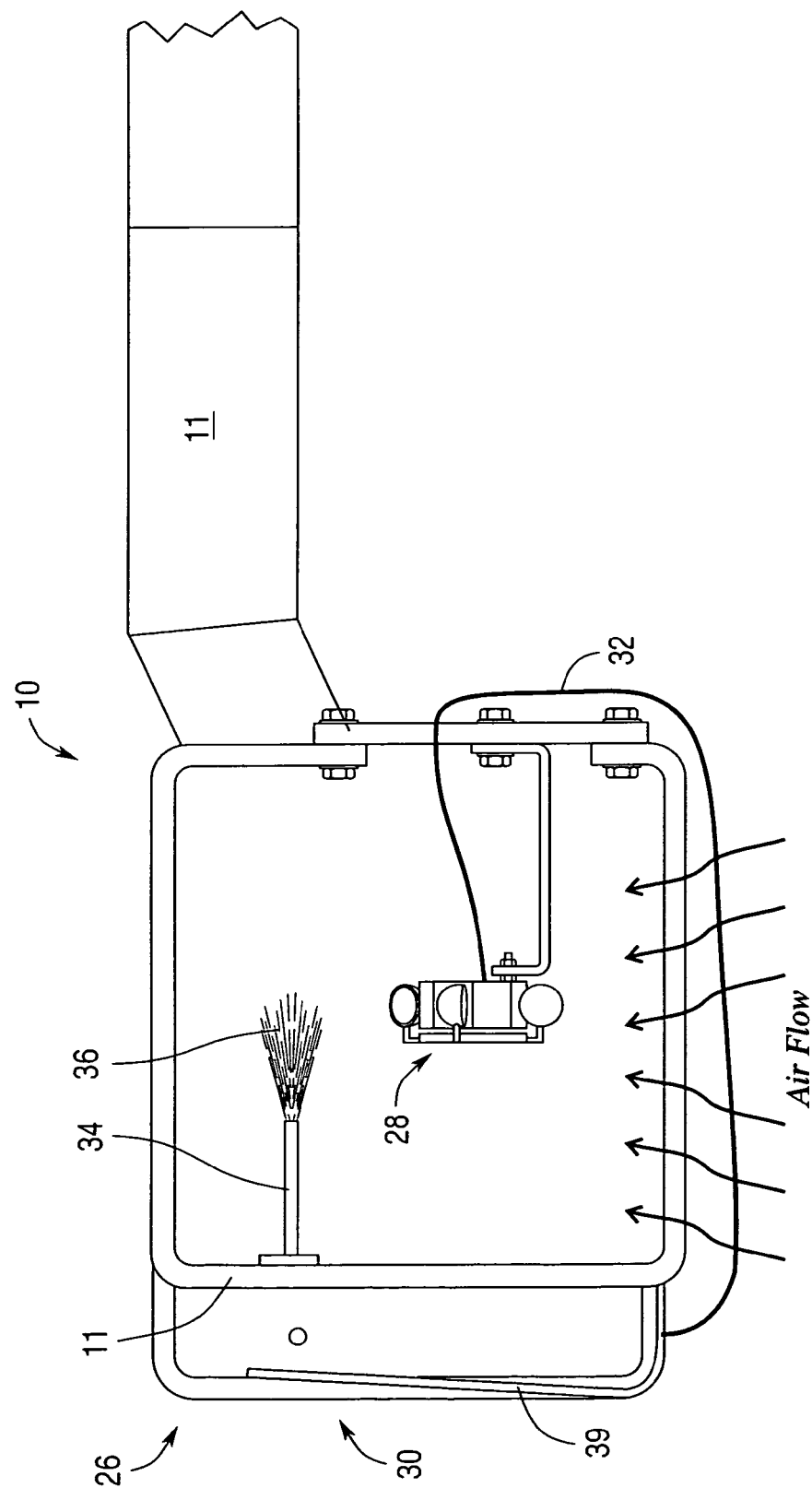
FIG. 2 is a schematic of the ductwork in a HVAC system illustrating a first positioning of a scent disperser arrangement of the invention.

FIGS. 2 through 5 illustrate various locations the scent disperser arrangement 26 of the invention may assume in an HVAC system 10. Referring to FIG. 6, the scent disperser arrangement 26 comprises a flow sensor 28, a scent disperser assembly 30, and an electrical connector 32 electrically connecting the flow sensor 28 to the scent disperser assembly 30. With particular reference to FIG. 2, the scent disperser arrangement 26 is positioned within the ductwork 11 of the HVAC system 10 away from the blower assembly 20 (FIG. 1).

As shown in FIG. 2, the flow sensor 28 is mounted through suitable means within the ductwork 11. Scent disperser assembly 30 is mounted outside the ductwork 11 and against an external wall surface 11a of the ductwork 11. In this embodiment, the scent disperser assembly 30 has an elongated tube 34 extending through its back cover (not shown). Tube 34 projects into the ductwork 11 for delivering a liquid scented spray 36 into the ductwork 11. The electrical connector 32 extends from the flow sensor 28 out along and beneath the ductwork 11 and to the scent disperser assembly 30. The air flow travels as indicated by the several arrows through the ductwork 11 and past the elongated tube 34 and flow sensor 28. This air flow which carries the scented spray 36 through the ductwork 11 passes across the flow sensor 28 to operate the flow sensor, more about which is discussed hereinafter.

Figure 3:
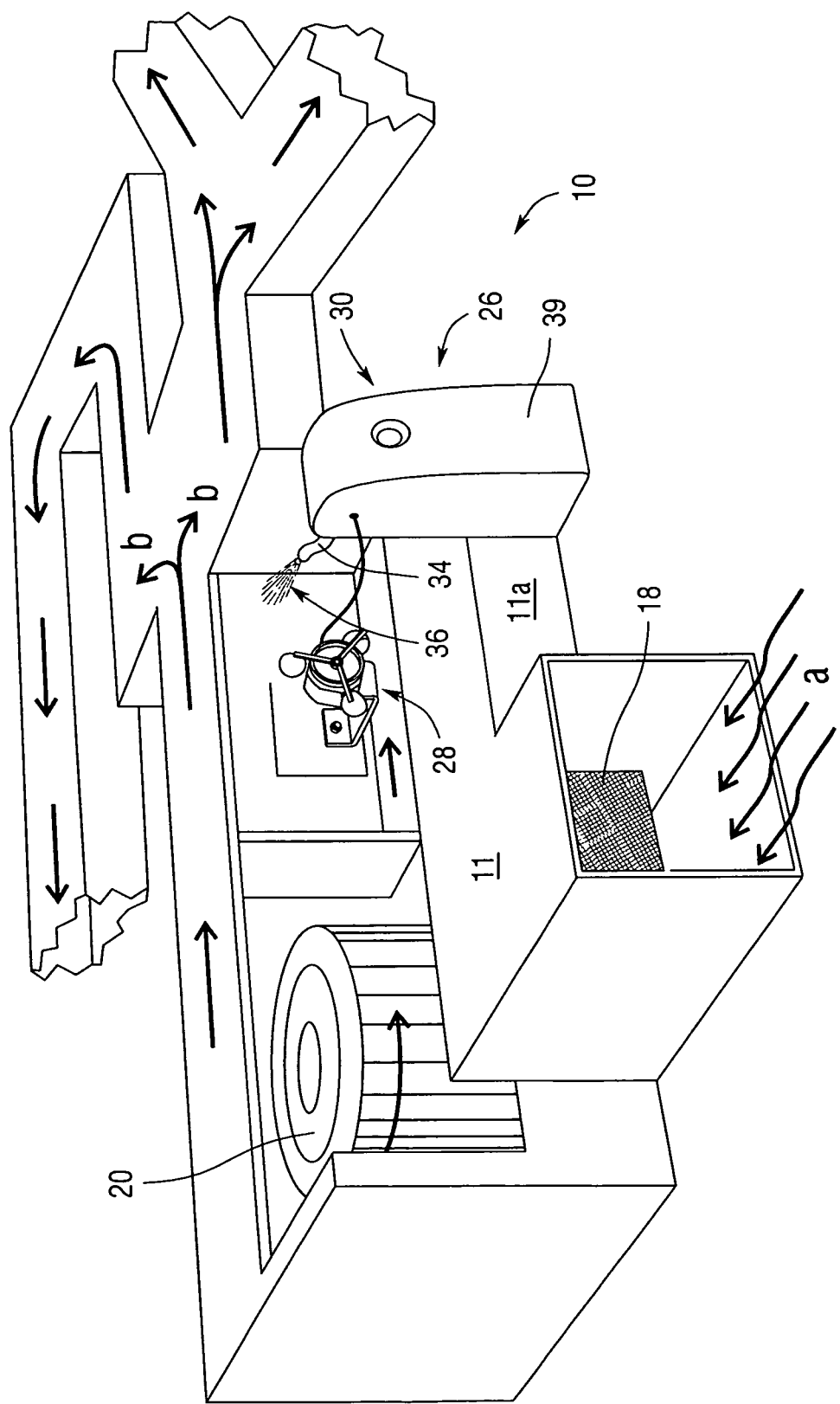
FIG. 3 is a schematic of an HVAC system illustrating a second positioning of the scent disperser arrangement of the invention.

FIG. 3 shows the scent disperser arrangement 26 positioned adjacent to the air blower 20. Here again, the flow sensor 28 is mounted within the ductwork 11 and the scent disperser assembly 30 is mounted to an external wall 11a of ductwork 11. In this embodiment, the elongated tube 34 extends through the back plate and into the ductwork 11 for delivering liquid scented spray 36 into the ductwork 11 which is then carried through the ductwork 11 by the air flow as shown by arrows b, and which air flow operates flow sensor 28.

Figure 4:
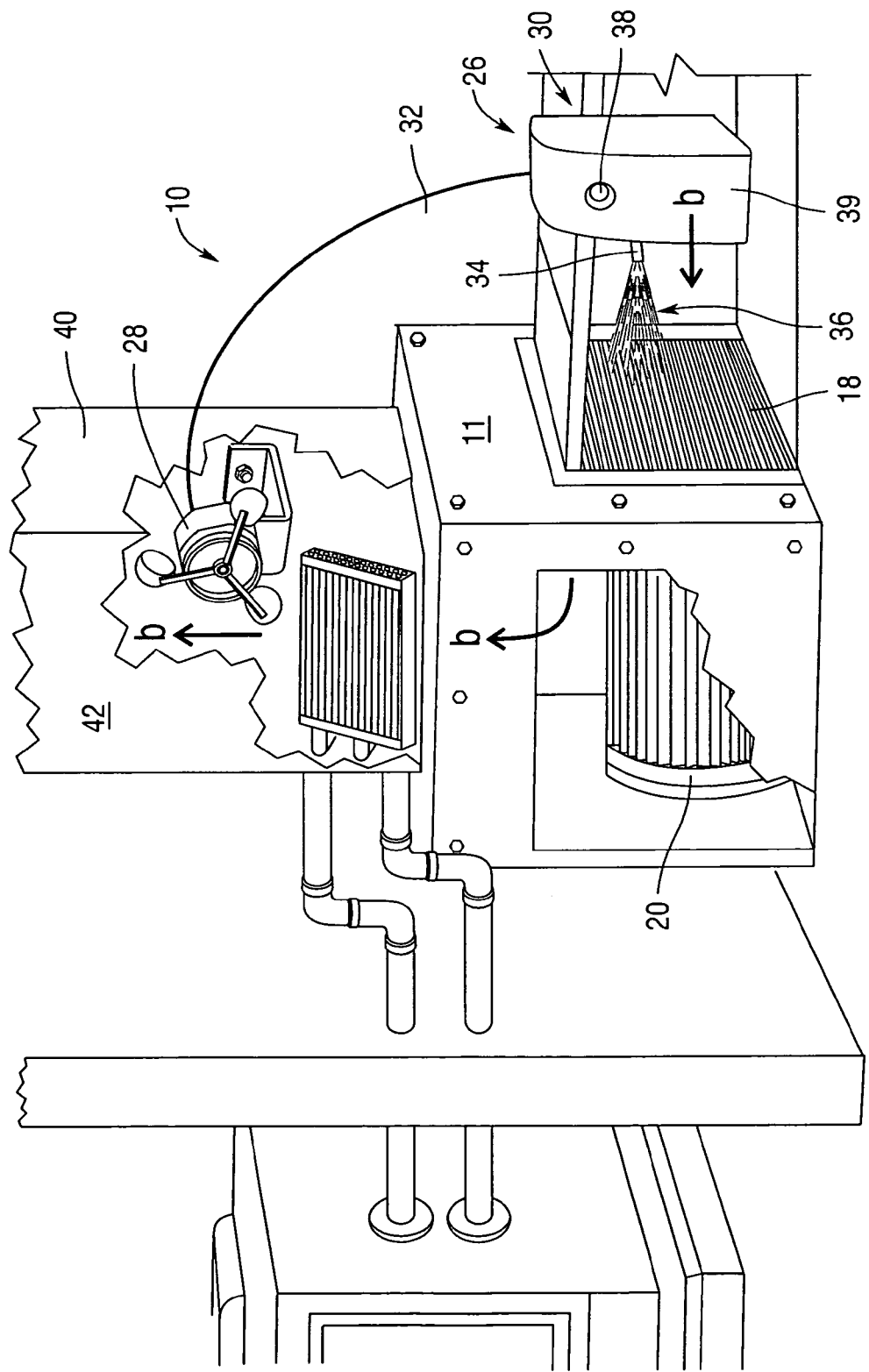
FIG. 4 is a schematic of an HVAC system illustrating a third positioning of the scent disperser arrangement of the invention.

FIG. 4 shows the scent disperser arrangement 26 positioned relative to an air handler 40 of the HVAC system 10. More specifically, the flow sensor 28 is mounted within section 42 of ductwork 11 of air handler 40 and the scent disperser assembly 30 is mounted in the ductwork 11 adjacent to the air filter 18. In this embodiment, elongated tube 34 extends through aperture 38 of front cover 39 of scent disperser assembly 30, while back plate (not shown) of scent disperser assembly 30 is mounted to an internal wall of ductwork 11. The scented liquid spray 36 is delivered through air filter 18, air blower 20, and air handler 40 as indicated by arrows b and then into the environment. Electrical connector 32 is connected to scent disperser assembly 30 and flower sensor 28 externally of the ductwork 11 and section 42 of air handler 40.

Figure 5:
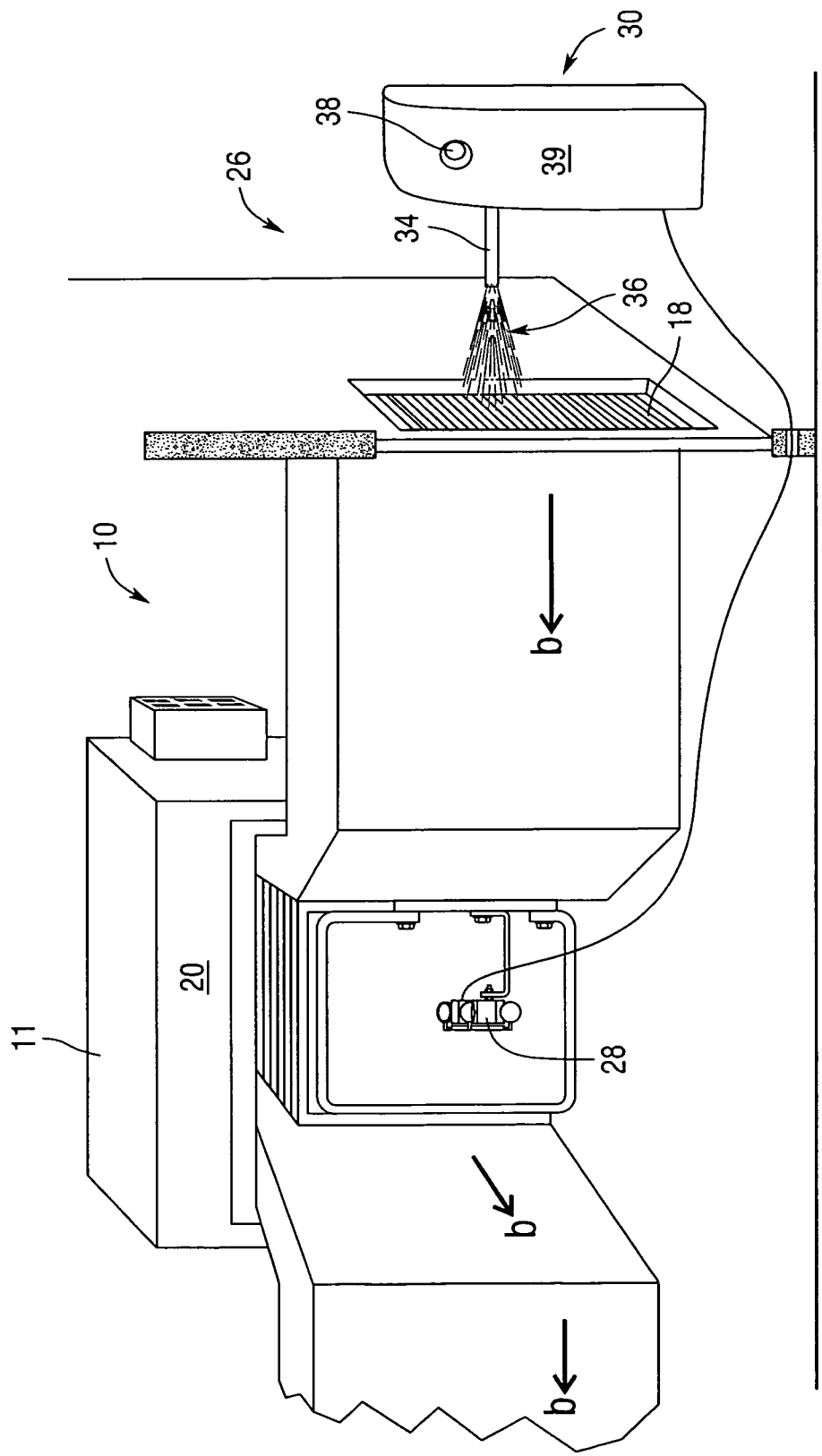
FIG. 5 is a schematic of an HVAC system illustrating a fourth positioning of the scent disperser arrangement of the invention therein.
Figure 6:
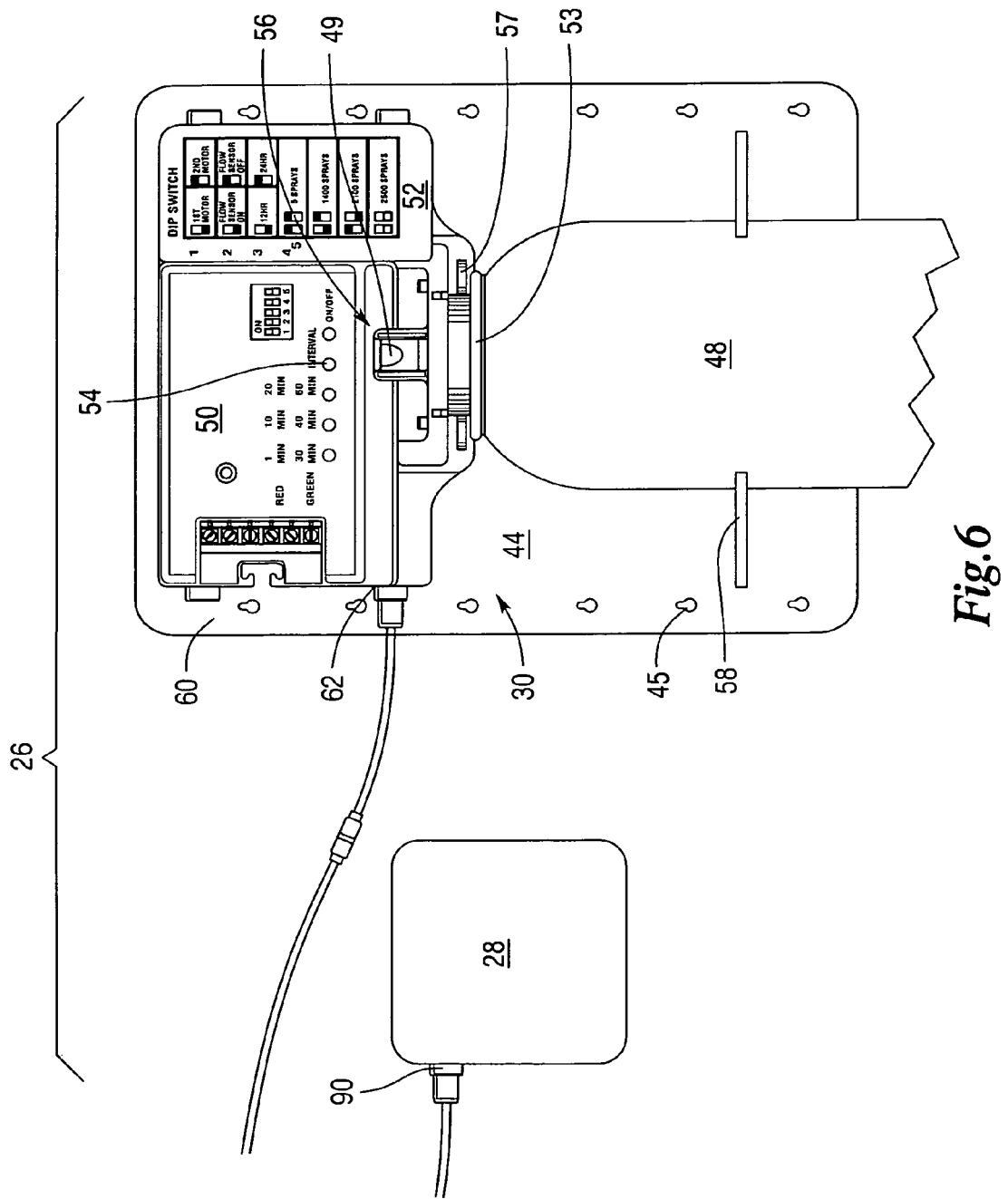
FIG. 6 is a partial front view of a flow sensor and a scent disperser assembly of the scent disperser arrangement of the invention with the front cover removed.

FIG. 5 shows the scent disperser arrangement 26 relative to air filter 18 where the scent disperser assembly 30 is floor mounted outside the air filter 18, and the flow sensor 28 is mounted at the outlet end of the air blower 20. The elongated tube 34 extends through aperture 38 of front cover 39 similar to that shown in FIG. 4, and the liquid scented spray 36 is directed into the air filter 18 and travels through the air blower 20, out of ductwork 11 and past flow sensor 28 as shown by arrows b.

Scent disperser assembly 30 may be of a powder coated carbon steel construction and as shown in FIGS. 2, 3 and 4 has a tapered body with a wide portion at the bottom and a narrow portion at the top but is not limited to that shape. Additional components of the scent disperser assembly 30 include a back plate 44 having an aperture cover 46 (FIG. 9) which can be punched out if elongated tube 34 is required to project out of back plate 44 for the required locating or positioning of scent disperser assembly 30 in the HVAC system 10 as discussed herein above and as shown, for example, in FIGS. 2 and 3.

Figure 7:
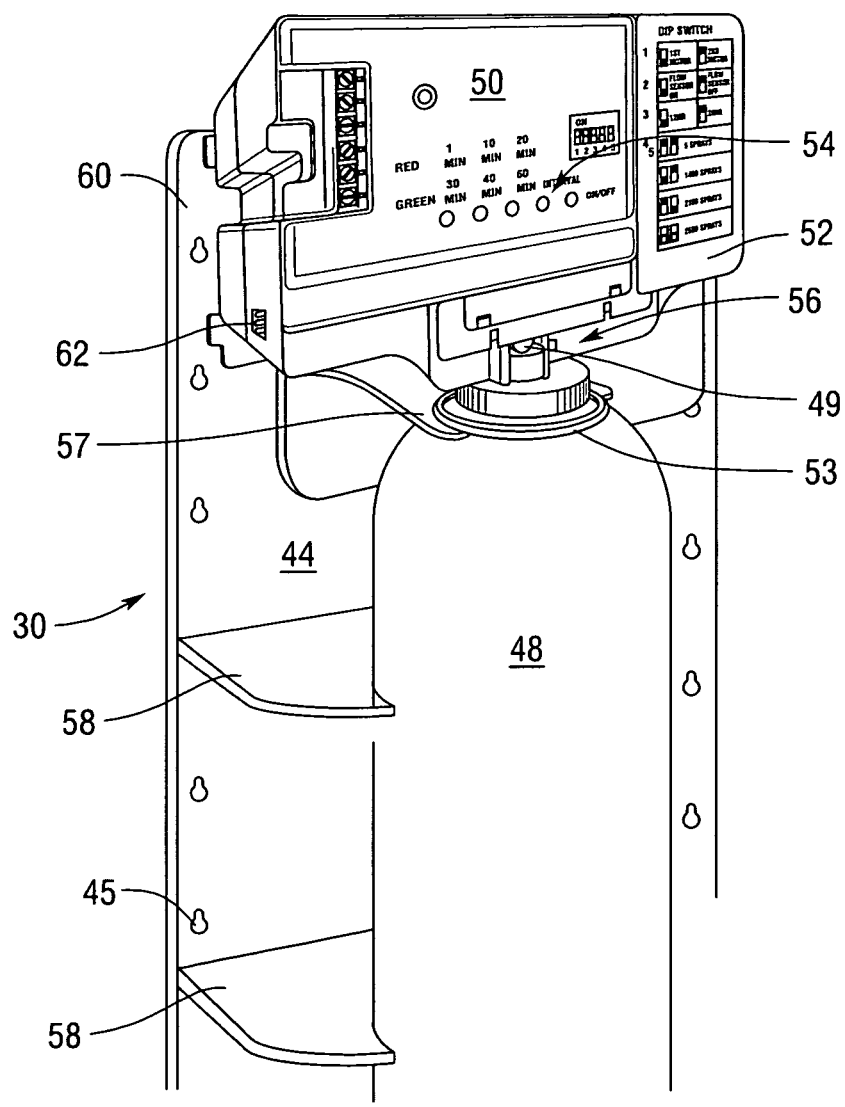
FIG. 7 is a left side perspective view of the scent disperser assembly of FIG. 6.
Figure 8:
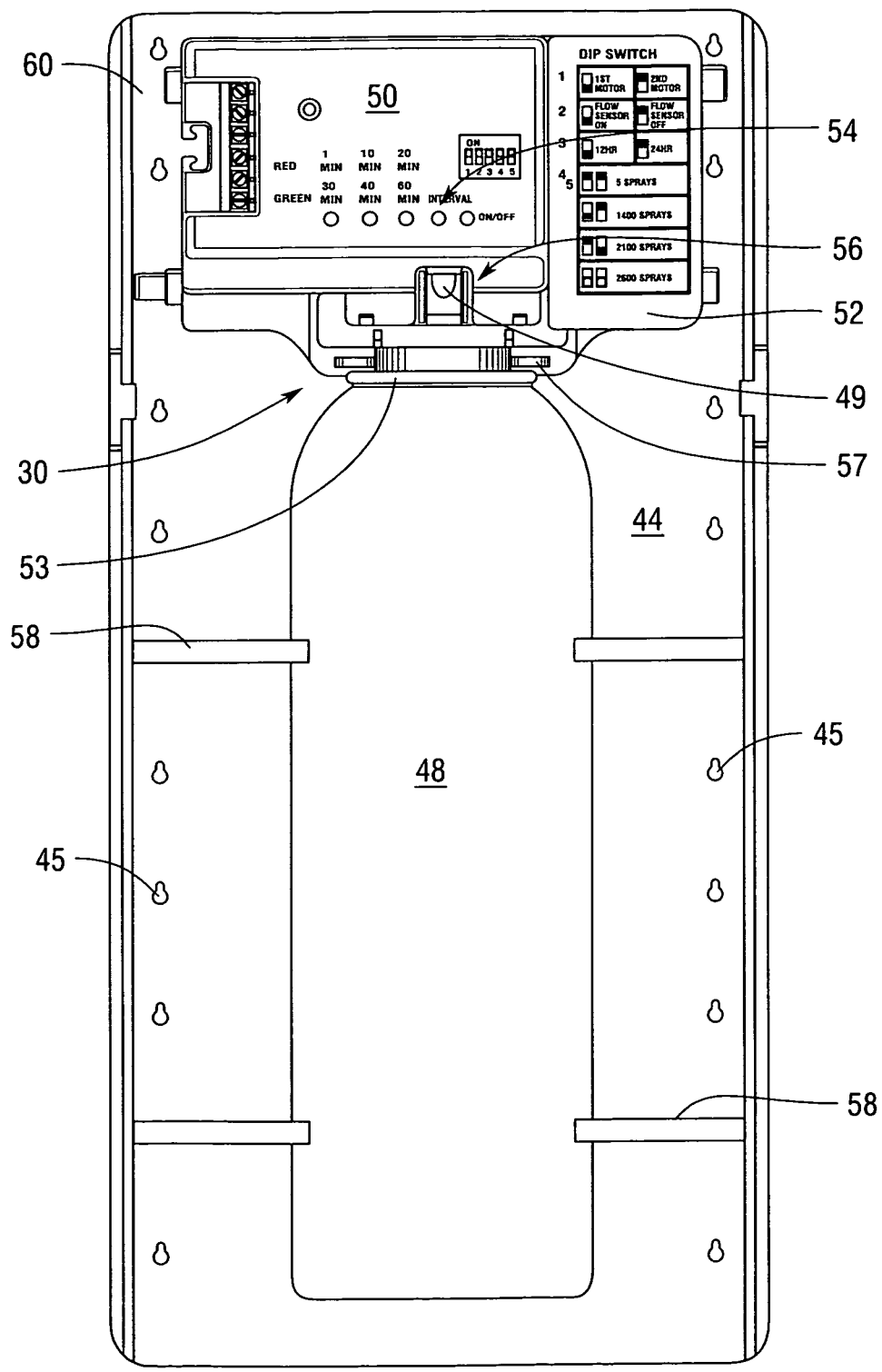
FIG. 8 is full front view of the scent disperser assembly of FIG. 6.
Figure 9:
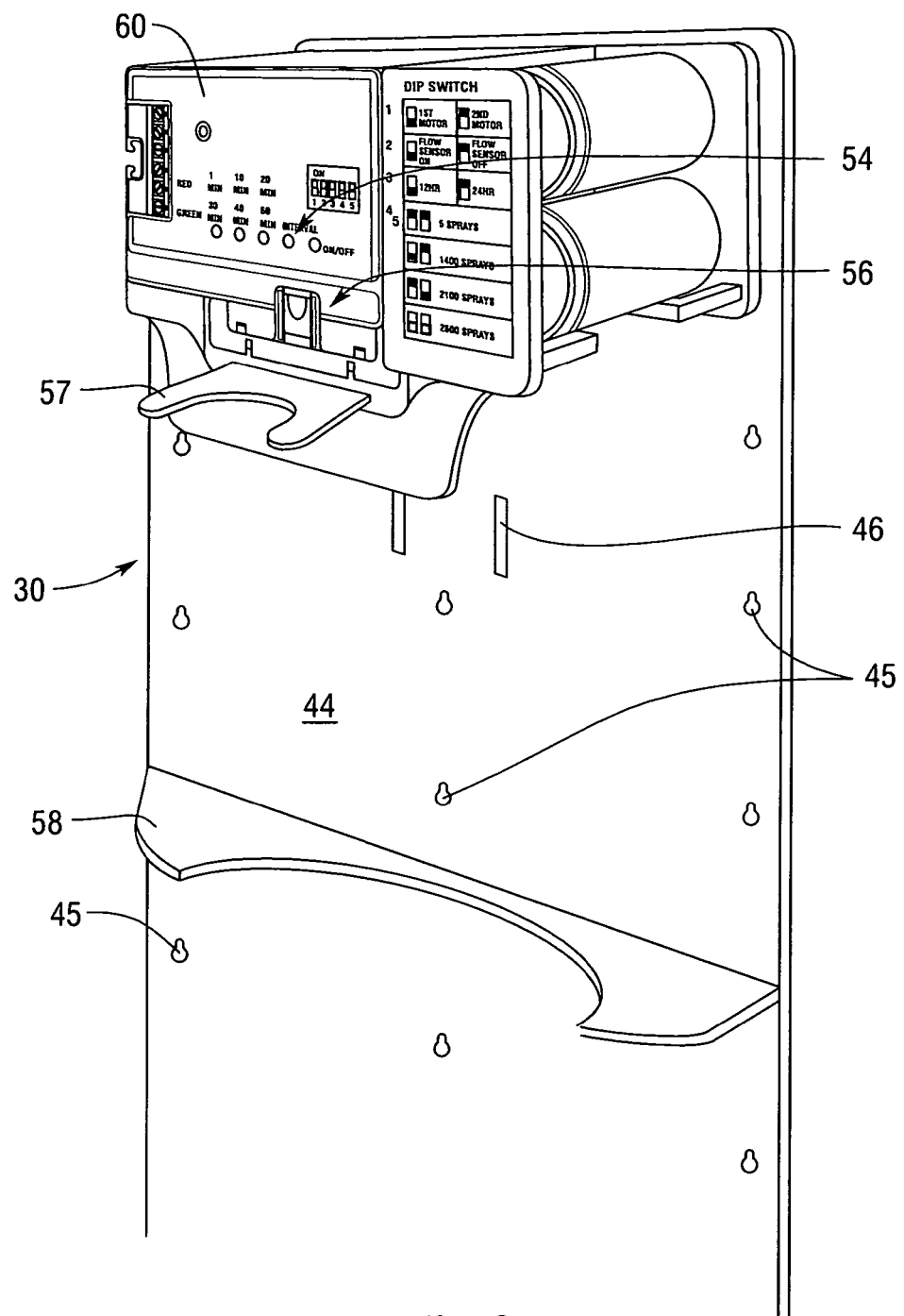
FIG. 9 is an enlarged partial right side perspective view of FIG. 8 showing a control module of the scent disperser assembly with the front cover and canister removed.
Figure 10:
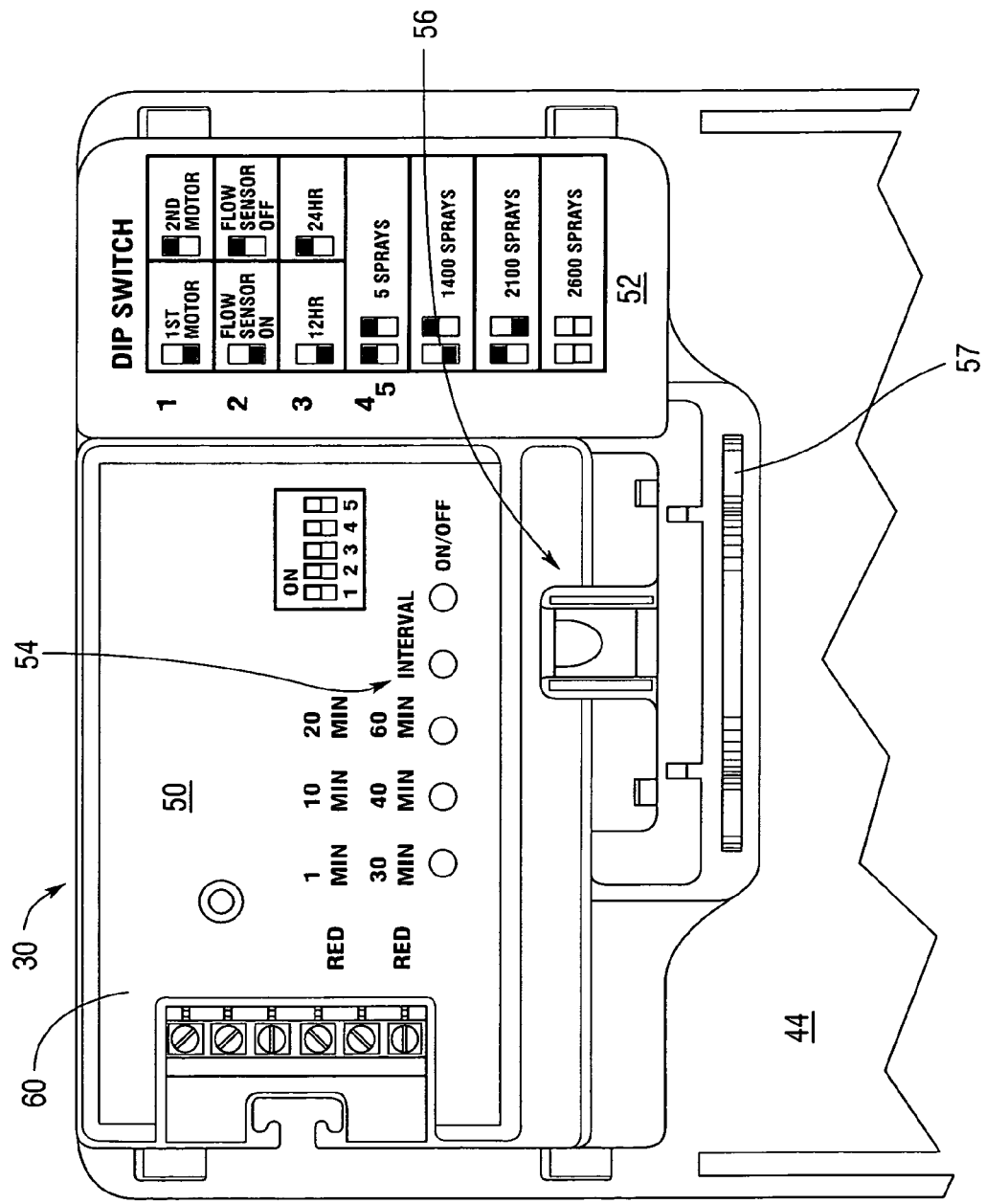
FIG. 10 is enlarged partial front view of FIG. 9 showing the control module.

FIG. 6 illustrates the flow sensor 28, scent disperser assembly 30 and electrical connector 32 of the scent disperser arrangement 26 of the invention while FIGS. 7, 8, 9 and 10 illustrate the components of the scent disperser assembly 30 without the front cover 39. Referring particularly to FIGS. 6, 7 and 8, scent disperser assembly 30 further comprises a canister 48 which contains a liquid fragrance and a control module 50, the latter of which is also shown in FIGS. 9 and 10. Control module 50 comprises a battery housing 52 for housing two C size batteries indicated by the letter "C" as best shown in FIG. 9. In general, control module 50 further comprises a controller 54 in the form of push buttons, which is digitally programmed and a plunger assembly 56 for activating actuator 49 (FIGS. 6, 7 and 8) which actuator 49 is mounted on top of canister 48. Even though not shown in FIGS. 6, 7 and 8, actuator 49 is in the form of an inverted "U" shaped member where the horizontal leg is adjacent to the plunger assembly 56 and the vertical legs snapped tightly onto the aerosol button of canister 48 in a manner well-known to those skilled in the art.

Plunger assembly 56 is powered by a motor (not shown) located in control module 50, for example, a 3-volt motor, to provide the force necessary to compress plunger assembly 56 against actuator 49 for operation of actuator 49, which delivers a scented spray of liquid. In some embodiments, controller 54 includes a computer program for delivering a desired number of fragrant liquid sprays per minute or hour. For example, controller 54 may be programmed to deliver six sets of fragrant liquid sprays per hour. For example, a fragrant liquid spray may be delivered every ten minutes, i.e. at 10 minute, at 20 minute, at 30 minute, at 40 minute, at 50 minute and at 60 minute settings within the hour. Even though not shown in FIGS. 6, 7 and 8, the elongated tube 34 of FIGS. 2-5 is inserted into actuator 49 for dispersing a fragrance into the HVAC system 10 through operation of actuator 49 by plunger assembly 56, as discussed herein above.

Still referring to FIGS. 6, 7, 8, and FIGS. 10, 10A and 10B, canister 48 and control module 50 fit snugly together when canister 48 is inserted into back plate 44. Canister 48 has an upper metal rim 53 adjacent to actuator 49 which is engaged by a bracket member 57 of control module 50 when canister 48 is inserted onto back plate 44. In this positioning of canister 48 on back plate 44, actuator 49 (see FIG. 8) is engaged in plunger assembly 56. As discussed hereinabove, actuator 49 retains elongated tube 34 of FIGS. 2-5. The structure of actuator 49 and plunger assembly 56 is such that if elongated tube 34 is inserted into aperture 46 (FIG. 9) of back plate 44, actuator 49 is engaged by plunger assembly 56 for operation thereof, and if the elongated tube 34 of canister 48 is inserted into aperture 38 of front cover 39 (FIGS. 2-5), actuator 49 is still engaged by plunger assembly 56 for activation of actuator 49 in delivering the scented liquid spray.

Support members 58 are provided for anchoring canister 48 on back plate 44 assembly. Support members 58 have an arcuate surface corresponding to the outer arcuate surface of canister 48 for spacing canister 48 away from back plate 44. Canister 48 is slid within back plate 44 in order to position the actuator 49 in alignment with either aperture 38 of front cover 39 or with aperture 46 of back plate 44. Elongated tube 34 is attached to actuator 49 of canister 48 so that it extends out of aperture 38 or out of aperture 46 for directing a fragrance spray out scent disperser assembly 30.

As particularly shown in FIGS. 6, 7 and 10, control module 50 further includes an electrical connection assembly 62 for electrically connecting the electrical connector 32 of FIG. 6 to control module 50 and flow sensor 28, more about which will be discussed herein after. In general, if flow sensor 28 is in an "on" mode, then flow sensor 28 is operated by air currents of the HVAC system 10 (FIGS. 1-5), which, in turn, causes operation of control module 50 according to the set up of control module 50 via the controller 54 and the computer program associated therewith, wherein plunger assembly 56 pushes down against actuator 49 to deliver the scented liquid spray into the HVAC system 10.

As shown best in FIGS. 8 and 9, back plate 44 includes several apertures 45 at different locations for attaching back plate 44 and therefore scent disperser assembly 30 to a flat surface, such as the external or internal walls 11a of the ductwork 11 of the HVAC system 10 of FIGS. 2-5, through suitable fastening means, such as, for example, screws or nails.

Figure 12:
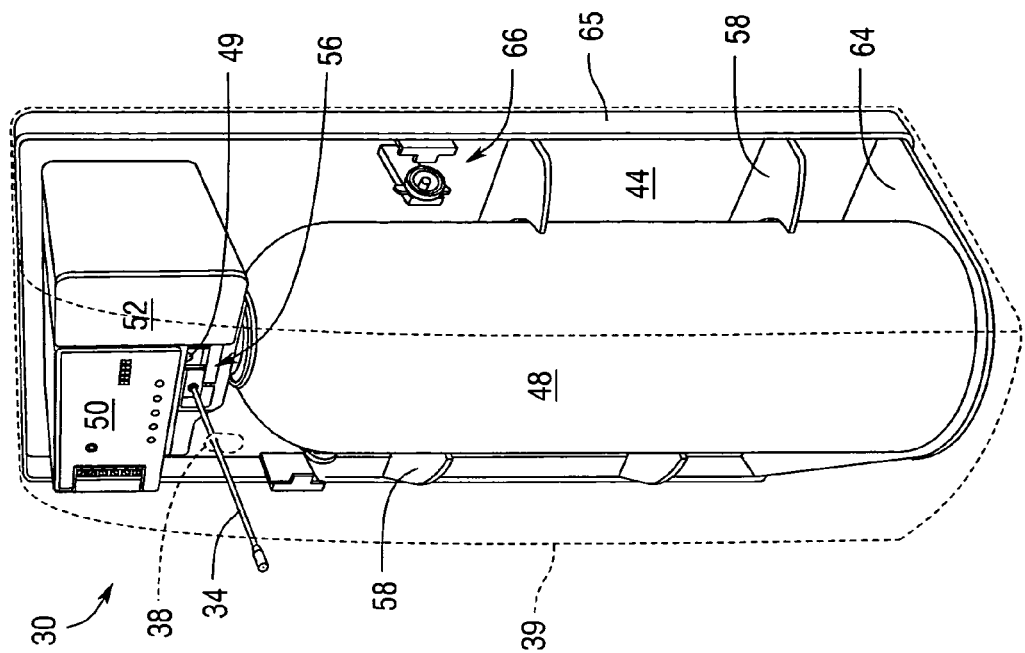
FIG. 12 is an enlarged perspective view of the scent disperser assembly partially of the invention showing the housing in phantom.

The canister 48 of FIGS. 6-9 may contain about 16 ounces of liquid; whereas the canister 48 of FIG. 12 may contain about 20 ounces of liquid. As shown in FIG. 12, canister 48 is supported at its bottom by support member 64 which has an arcuate surface essentially corresponding to that of canister 48. Still referring to FIG. 12, back plate 44 has a ledge 65 which essentially extends around the entire perimeter of back plate 44 so that front cover 39 can be set into and positioned within this ledge 66 for attachment of front cover 39 to back plate 44.

In the design of the scent disperser assembly 30 of FIG. 12, front cover 39 is located and secured to the side of back plate 44 via a tubular key cam lock and lock catch assembly 66 shown best in FIG. 12. Key cam lock and lock catch assembly 66 comprises a lock pawl (not shown). The lock pawl is rotated via rotation of a key cam lock-lock catch assembly 66, and engages a lock catch pin (not shown) in a bracket of back plate 12 in a manner well-known to those skilled in the art. Tubular key cam lock and lock catch assembly 66 requires a key for operation. Tubular key cam lock and lock catch assembly 66 is commercially available and its operation is well-known to those skilled in the art. A handle maybe attached to the top of front cover 39 for easy toting of scent disperser assembly 30.

Figure 13:
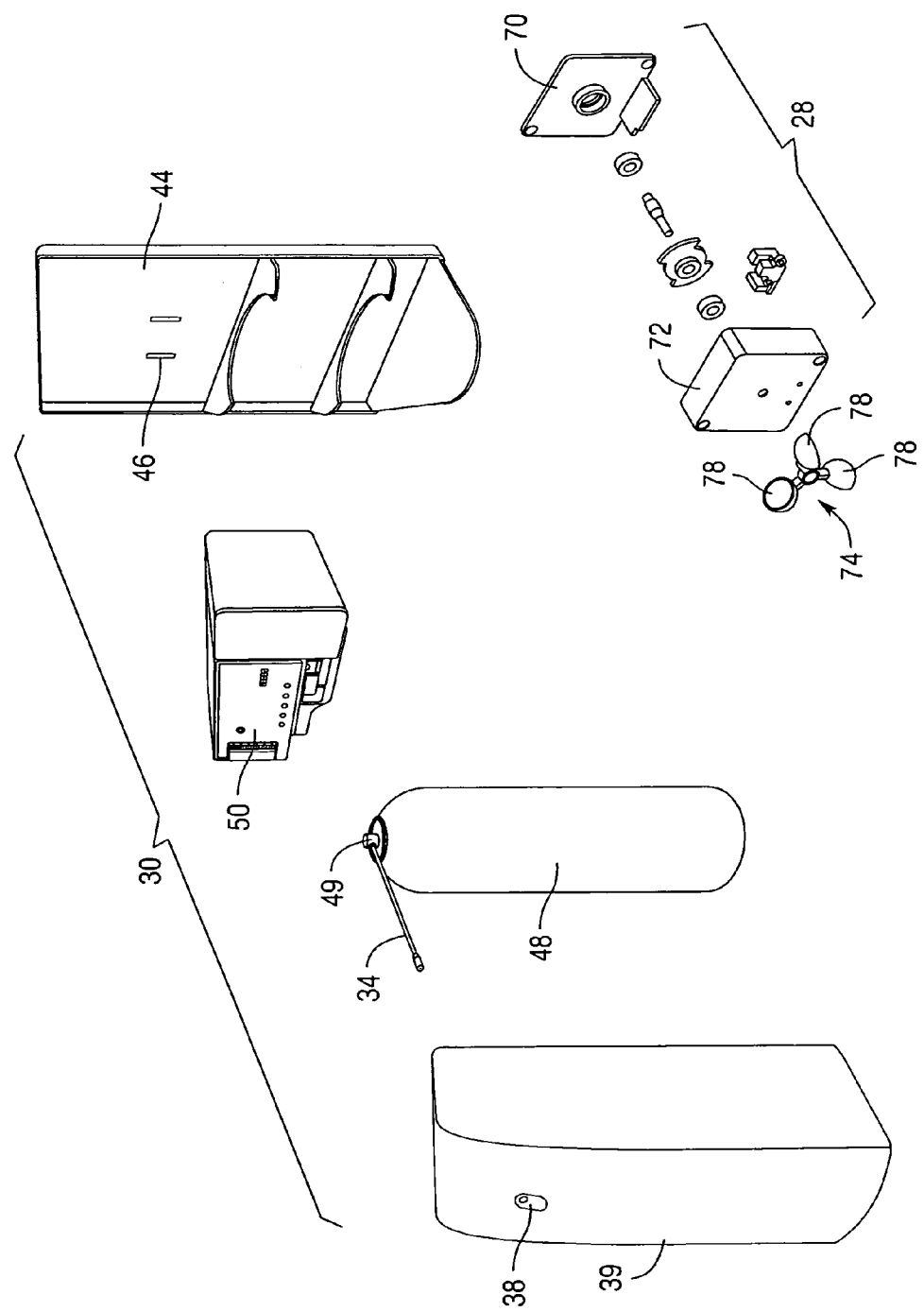
FIG. 13 is an exploded perspective view of the scent disperser assembly partially in schematic and the flow sensor of the scent disperser arrangement of FIG. 6.
Figure 15:
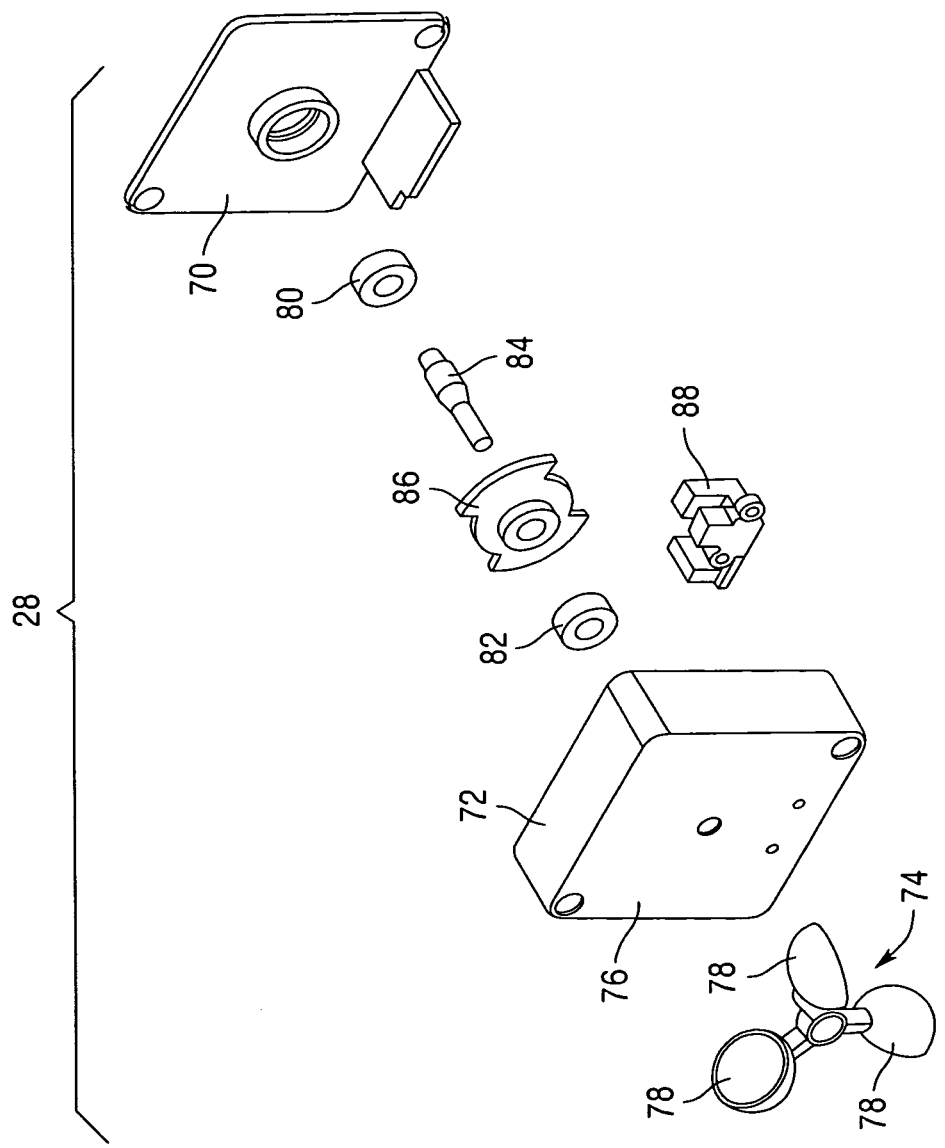
FIG. 15 is an exploded, enlarged perspective view of the flow sensor of the scent disperser arrangement of the invention.
Figure 16A:
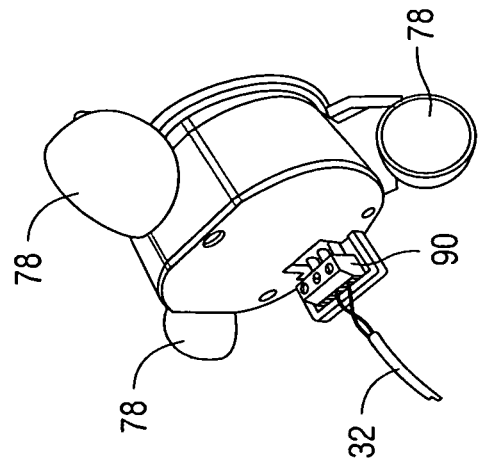
FIG. 16A is a perspective view of the flow sensor looking from its rear.
Figure 16:
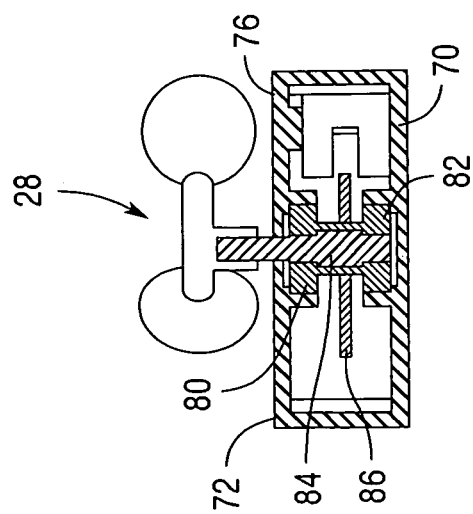
FIG. 16 is a sectional view of the flow sensor of the invention.

Referring now to FIG. 13, scent disperser assembly 30 and flow sensor 28 are shown in an exploded view. The components of scent disperser assembly 30 have already been discussed with reference to FIGS. 6-10. The components of flow sensor 28 will be discussed with particular reference to FIGS. 11, 13, 15, 16 and 16A. As better shown in FIGS. 15 and 16A, flow sensor 28 comprises plate member 70, housing 72 and a rotatable member 74 that is attached to the external surface 76 of housing 72. Rotatable member 74 comprises a plurality of cup elements 78. Rotation of rotatable member 74 is effected via bearings 80 and 82, shaft 84, cam 86, and a seating member 88 for positioning bearings 80 and 82; shaft 84, and cam 86 within plate member 70 and housing 72, as better shown in FIG. 16. As shown in FIG. 16A, flow sensor 28 also includes an electrical connection. In general, the flow sensor comprises an anemometer having the plurality of cup elements 78 and which is rotatably mounted on the flow sensor for detecting air flows to cause the cup elements 78 to rotate and to create the electrical signal of the flow sensor which is transmitted to the control module 50 of the scent dispenser assembly 30. An electrical connection in the form of a voltage signal connects the flow sensor 28 to the electronic module 52 of the scent dispenser assembly 30. The electronic module 52 comprises a computer program for selectively operating the canister for dispensing the scented spray.

In operation, the rotatable member 74 is rotated by the air currents in the HVAC system 10 (FIGS. 2-5). In this process, cup elements 78 catch the air currents and rotation of the rotatable member 74 sends this information to control module 50 of scent disperser assembly 30 for operation of canister 48 according to the set up of control module 50 via controller 54. That is, when the air flow rotates cup elements 78, an electrical signal is generated and is sent through the cable 32 and to control module 50. This signal continuously sends pulse information to control module 50 to provide the voltage for plunger assembly 56 to mechanically move up and down for operation of the scent disperser assembly 30.

Figure 11:
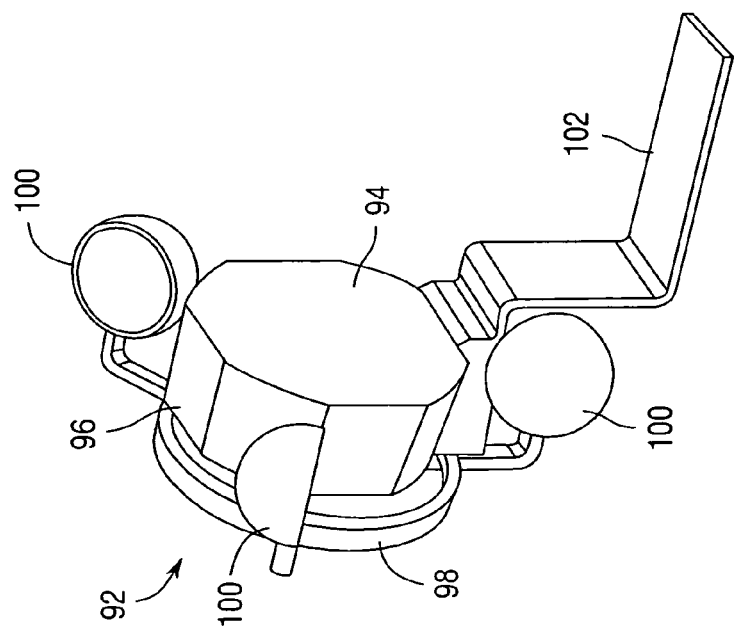
FIG. 11 is an enlarged perspective view of the flow sensor of the scent disperser arrangement of the invention.

FIG. 11 shows a further embodiment of a flow sensor 92 wherein plate 94 and housing 96 have a octagonal configuration, rotatable member 98 has a circular configuration and cup elements 100 extend from the circular configuration. In this embodiment, a bracket 102 is provided for mounting the flow sensor 92 or 28 inside the ductwork 11 of the HVAC system of FIGS. 2-6. Bracket 102 may be attached to a plate, which in turn is attached to the ductwork 11, or bracket 102 may be directly attached to the ductwork 11 of the HVAC system 10 of FIGS. 2-5.

FIGS. 14A, 14B, 14C, 14D and 14E show various views of the scent disperser assembly 30 and its components within front cover 39. This structure 30 will be preferably used when back plate 44 is mounted against a wall of ductwork 11 (FIGS. 2-4).

Figure 17:
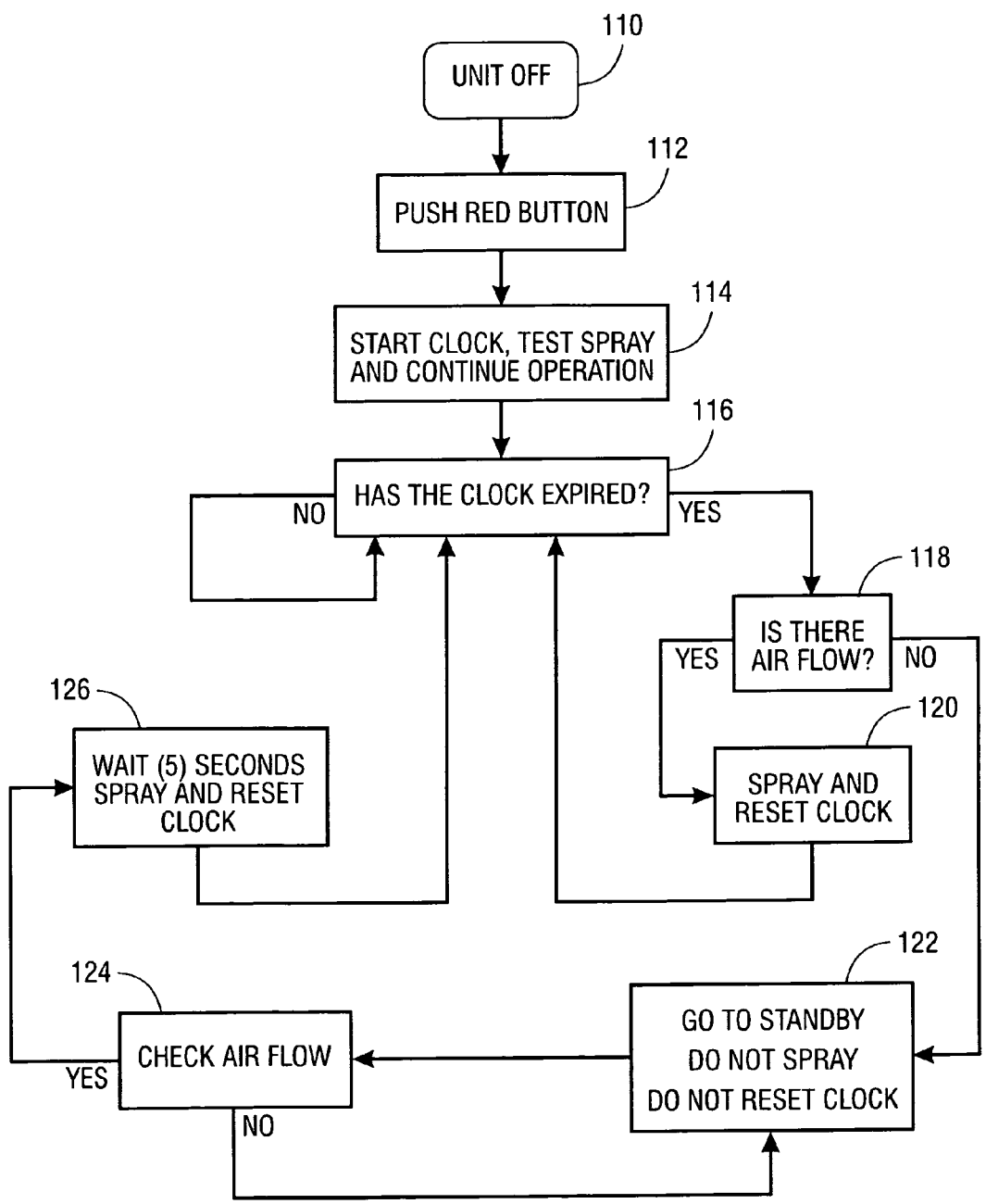
FIG. 17 is a flow diagram for operating the scent disperser assembly.

FIG. 17 illustrates an example of a flow chart for a computer program for operation of control module 50 of FIGS. 6-10. As shown, in step 110 the unit or control module 50 is in an "off" position. In step 112, one or more buttons of controller 54 are pushed in for a 10, 20, 30, 40, 50, or 60 minute interval and for operation in either the morning (a.m.) or evening (p.m.). These designations will be identified on the controller 54 in association with the red buttons of controller 54. Step 114 indicates that a clock in the computer program will be started, a spray will be tested, and the plunger assembly 56 and actuator 49 will continue to be operated. In step 116, the question is asked whether the clock has expired. If the answer is "No", the program continues to run in its current mode. If the answer is "Yes", the program moves to step 118 which asks the question: "Is there an air flow?" This air flow is generated within the HVAC system 10 and detected by flow sensor 28. If the answer is "No", then the computer program moves to step 120 which informs the computer program of control module 50 to go to standby, do not spray, and do not reset the clock. If the answer in step 118 is "Yes", then the computer program goes to step 122 which tells the computer program to spray and reset the clock. Step 120 goes to step 124 which checks the air flow in the HVAC system 10 detected by the flow sensor 28. If there is no air flow, the computer program continues to go to step 122. If there is an air flow in the HVAC system 10, the computer program goes to step 126 which tells the computer program to wait 5, 10, 20 minutes, etc. whatever set up was initiated by controller 54, and to start operation of the plunger assembly 56 and actuator 49, and then to reset the clock for the next minute interval. Step 126 then leads back to step 116 until the clock for the session keyed into controller 54 of scent disperser arrangement 26 has expired. By way of Example, should vent flow intervals be set for say 40 minute start-stop, flow emitted and ceased, cycles, and should air flow stop interrupting the cycle and within a ceased flow of scent fragrance interval, the scent disperser assembly 30 is deactivated and upon resumption of air flow the scent disperser assembly 30 is activated and the timed cycle is resumed from the beginning of the timed interval. In other words, the timed interval begins again from the beginning of the interval. By way of further example, should air flow stop in a 40 minute start-stop, flow emitted and ceased cycles, interrupting the cycle and within an emitted flow of scent fragrance interval, the scent disperser assembly 30 is deactivated and flow of scent fragrance ceased, and upon resumption of air flow the scent dispenser assembly 30 is activated and the timed cycle is resumed with emitted flow of scent fragrance resumed at the point of time when it ceased.

Figure 18:
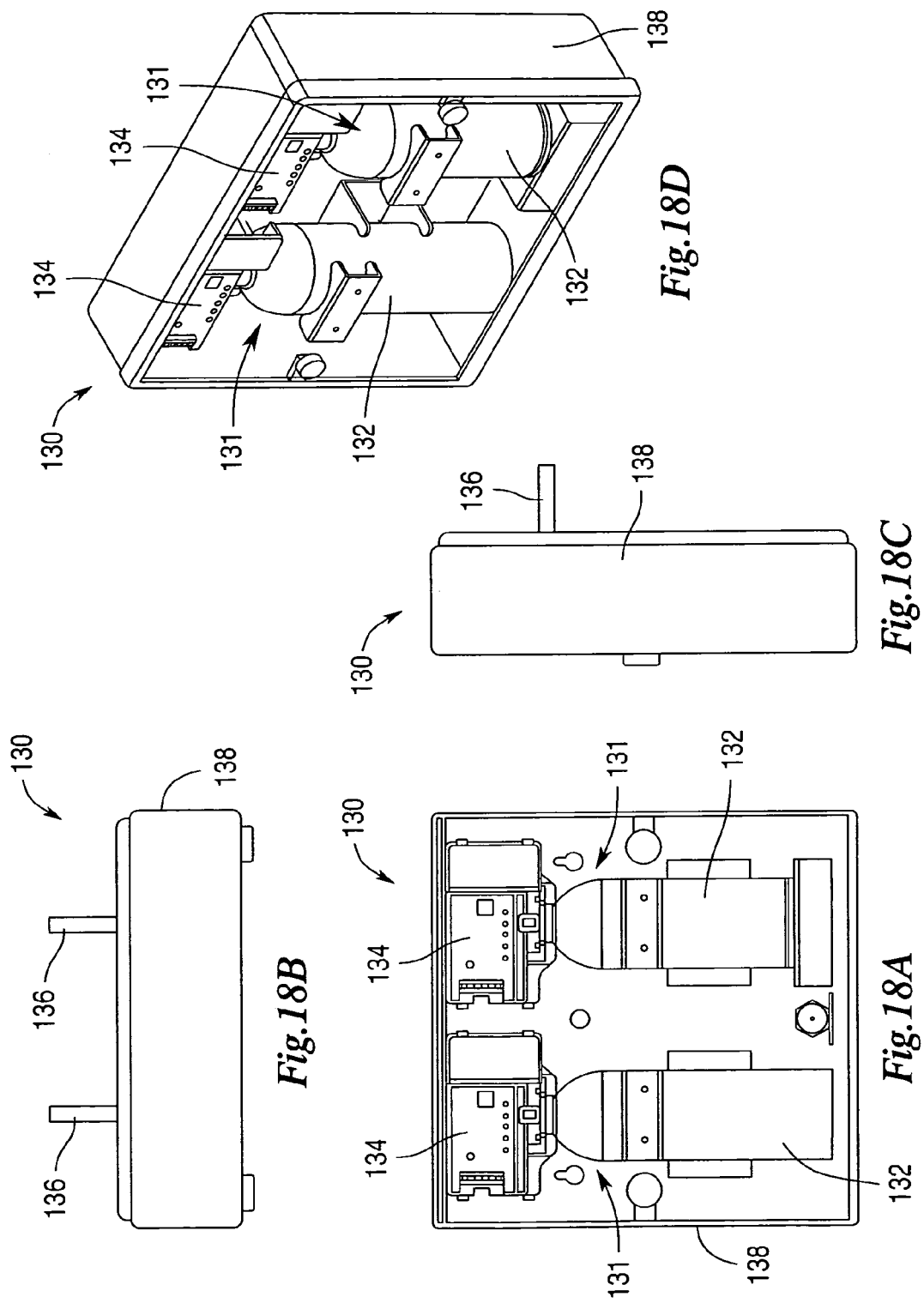
FIG. 18A is a schematic front view of a further embodiment of a scent disperser assembly of the invention.
FIG. 18B is a schematic top view of the scent disperser assembly of FIG. 18A.
FIG. 18C is a schematic side view of the scent disperser assembly of FIG. 18A.
FIG. 18D is a schematic perspective view of the scent disperser assembly of FIG. 18A.

FIGS. 18A, 18B, 18C and 18D illustrate a housing arrangement 130 which contains two scent disperser assemblies 131. Each scent disperser assembly 131 comprises a canister 132 and a control module 134. The construction and operation of each scent disperser assembly 131 is similar to scent disperser assembly 30 of FIGS. 6-10, the difference being that the control modules 134 of scent disperser assembly 131 can be set up to be controlled in series, that is, when one canister 132 is depleted or upon the first scent disperser 130 spraying a predetermined number of sprays, the adjacent canister 132 can then be operated to deliver a required amount of sprays, or while the depleted canister 132 can be replaced. In this embodiment, the elongated tube or spray nozzle 136 extends out of the back of housing 138 as best shown in FIGS. 18B and 18C. With regard to FIG. 18A, and by way of example, the canister 132 to the right may contain about 16 ounces of scented liquid and is supported by a platform 140 and the canister 132 to the left may contain about 20 ounces of scented liquid and is supported directly by housing 138. In an obvious manner, housing 138 is enclosed by providing a plate (not shown) which is attached to housing 138, and which plate can be conveniently removed for setting up control modules 134 for operation of canisters 132. The housing or cabinets for the scent disperser assemblies of the invention may be made of a suitable material, such as, for example, plastic, aluminum and metal.

Figure 19:
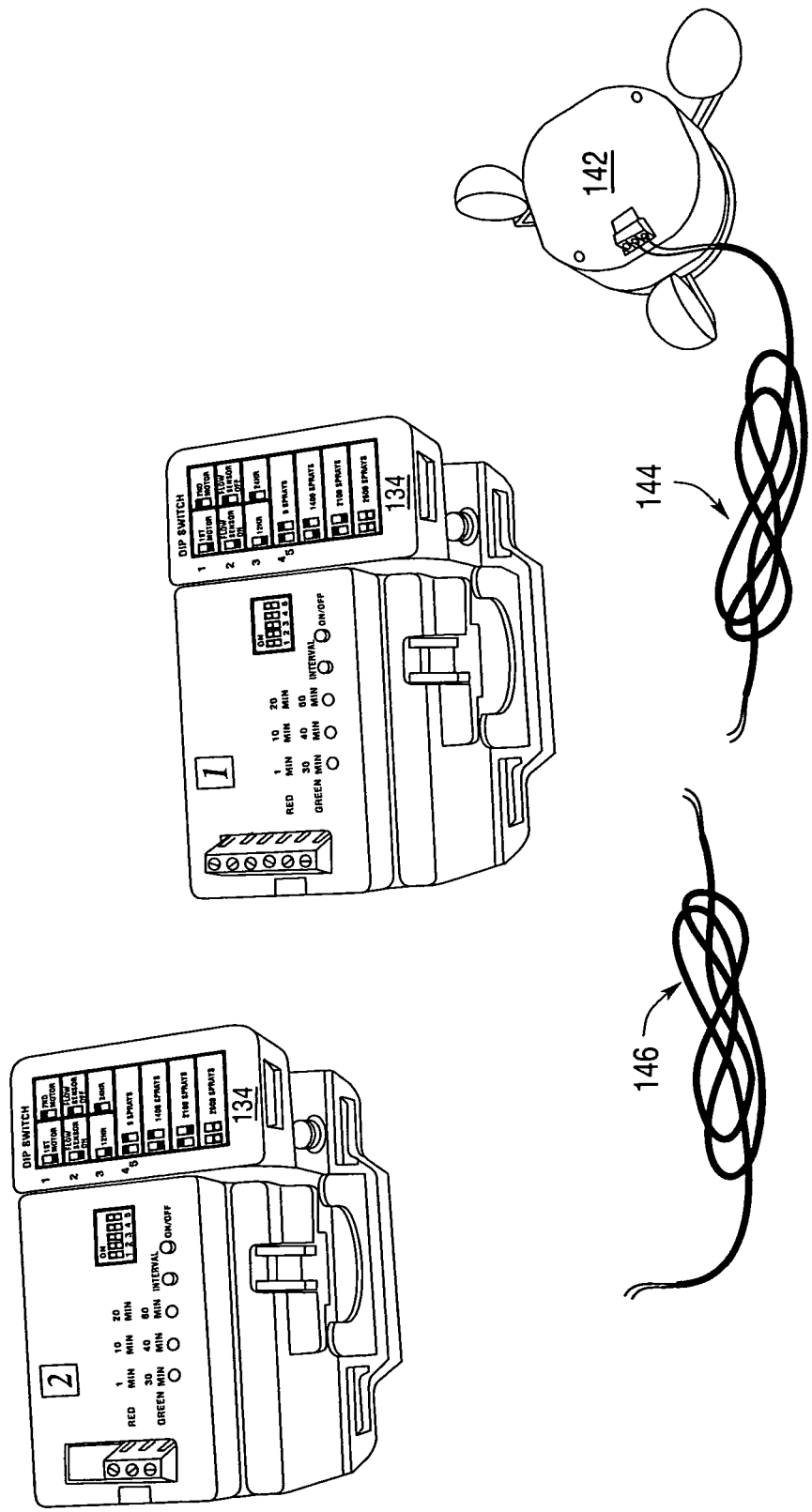
FIG. 19 are perspective views showing the two control modules of the scent disperser assembly of FIG. 18A, flow sensor and wiring of the scent disperser arrangement of the invention.

FIG. 19 more clearly illustrates the two control modules 134 for canisters 132, a flow sensor 142, electrical connector 144, and additional wiring 146 for electrically connecting the two control modules 134 together and with flow sensor 142. As shown in FIG. 19, the control module 134 to the right contains the number "1" and the control module 134 to the left contains the number "2". These are indicated as such for easy identification of these modules in explaining aspects of the invention, more about which is discussed herein below.

Figure 20:
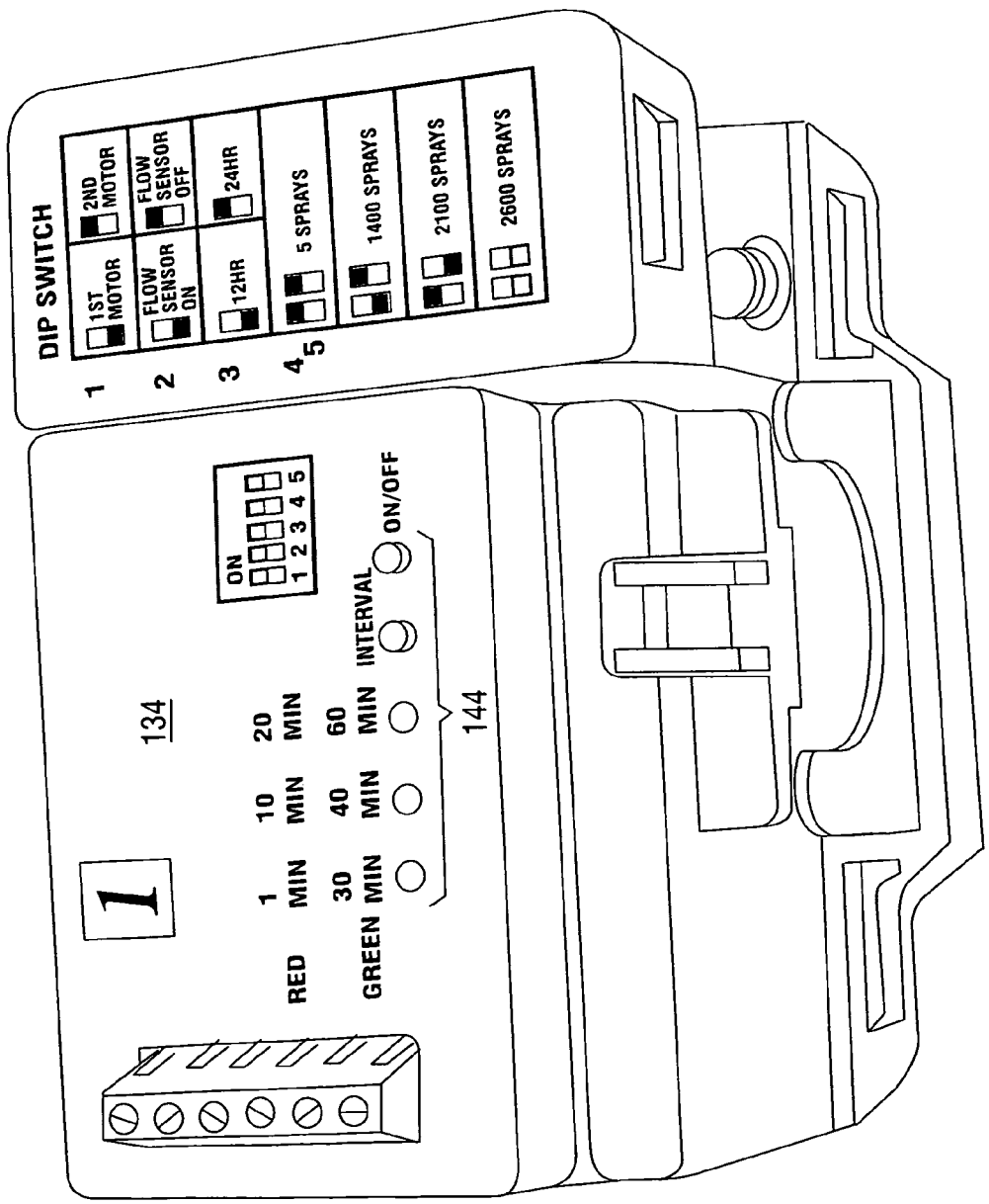
FIG. 20 is an enlarged perspective view of a first control module of the scent disperser assembly of FIG. 19.
Figure 21:
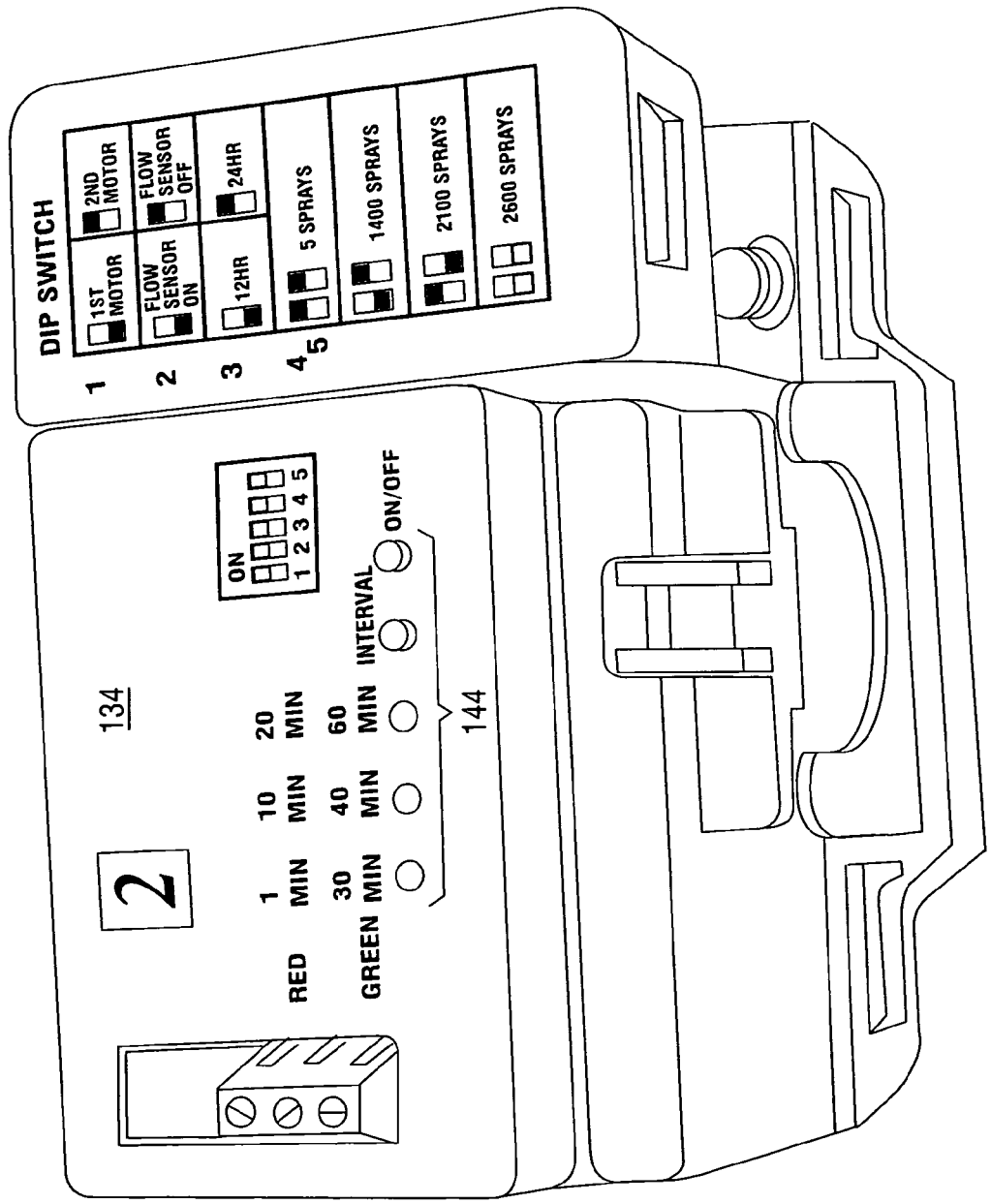
FIG. 21 is an enlarged perspective view of a second control module of the scent disperser assembly of FIG. 19.

FIGS. 20 and 21, respectively, are enlarged views of the control modules 134 wherein control module 134 of FIG. 20 contains the number "1" and the control module 134 of FIG. 21 contains the number "2". In FIG. 20, the front surface of control module 134 contains a controller 144 containing five push buttons and a toggle switch panel with 4 toggles. To the far left of control module 134 of FIG. 20 are six electrical plug receptacles wherein the first top three prong receptacles are for connecting the first motor of module 134 to the flow sensor 142 (FIG. 19), and the last bottom three prong receptacles on each control module 134 are for linking the motor of each control module 134 together. To the right of these receptacles is an LED 148.

Figure 23:
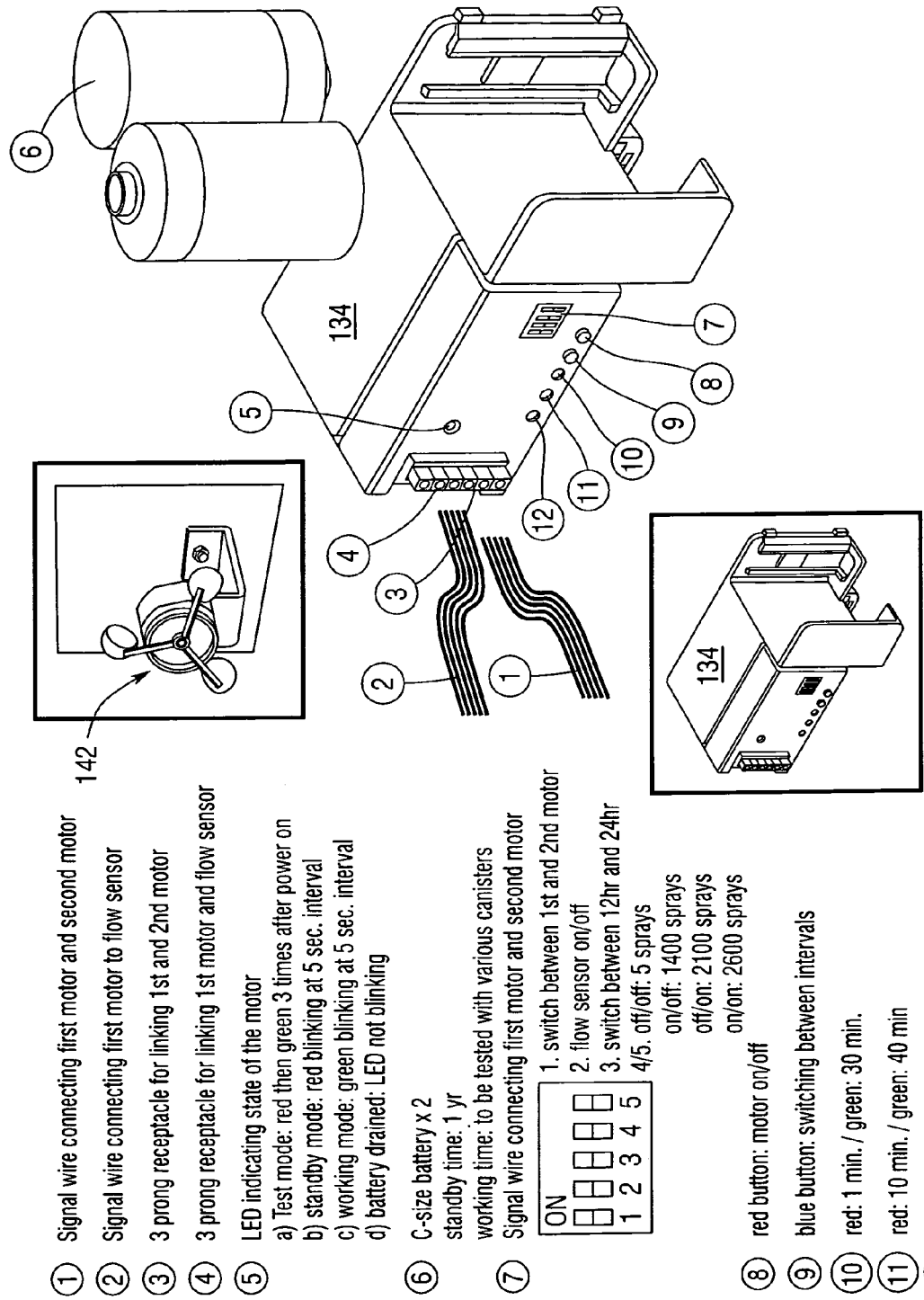
FIG. 23 is a schematic of the two modules of FIG. 19 and a diagram for electrically connecting the two control modules and the flow sensor.

Still referring to FIGS. 20 and 21, controller 144 further includes indicia for the five push buttons. These buttons and the interconnection of control modules 134 with each other and with flow sensor 142 of FIGS. 19 through 21 are better appreciated with reference to FIGS. 22 and 23. With reference to FIG. 23, reference number 1 indicates that the signal wire is for connecting the first motor and the second motor of control modules 134 together. Reference number 2 indicates that the signal wire connects the first motor of the control module 134 containing number "1" to the second motor of the control module 134 containing number 2. Reference number 3 indicates three prong receptacles for linking the two motors together. Reference number 4 indicates three prong receptacles for linking the first motor to the flow sensor 142. Reference number 5 indicates an LED on control module 134, more about which will be discussed herein below. In addition to an LED, an LCD display may also be provided on the face of control module 134, which may display the pertinent information for operation of the scent disperser assembly 131.

Reference number 6 indicates two size C batteries. Reference number 7 indicates the toggle panel on the front of canister 132. Reference number 8 indicates a red button wherein the motor can be on or off. Reference number 9 indicates a blue button, which can be switched between intervals. Reference number 10 indicates that this button can be red for 1 minute/green for 30 minutes. Reference number 11 indicates that this button can be red for 10 minutes/green for 40 minutes. Reference number 12 indicates that this button can be red for 20 minutes/green for 60 minutes.

Referring again to FIGS. 20 and 21, the five push buttons can be set up similar to that of FIG. 23. In these FIGS. 20 and 21, the first button to the right is an on/off button. Next to this button and moving to the left of these figures is the "Mode" button. Next to this button and still moving to the left, is a button which can be red for 30 minutes and green for 60 minutes, and consecutively, the next button can be red for 20 minutes and green for 50 minutes, and the next button can be red for 10 minutes and green for 40 minutes. This entire set up depends on the amount of sprays desired in a selected time interval, and whether the sprays should be operated in the morning or in the evening. The toggle panel provides for one or more of these features. Referring again to FIGS. 22 and 23, toggle switch "1" is operated to switch between the first motor and the second motor. Toggle switch "2" is operated to turn the flow sensor 142 on or off. Toggle switch "3" is operated to control when the sprays are to be operated which can be either in a 12 hour interval or in a 24 hour interval. Toggle switches "4" and "5" are operated to control the number of sprays. As indicated on FIGS. 20-23, operation of the last two toggle switches "4" and "5" can obtain either 5 sprays in the desired interval; 1400 sprays in a desired interval; 2100 sprays in a desired interval; or 2600 sprays in a desired interval for each canister 132.

Referring specifically to FIG. 23, the LED reference number "5" represents several operating modes. A test mode is represented when the LED it first "red" followed by three blinking green lights and occurs when the power is initially turned on. A standby mode is represented by the LED blinking "red" at 5 second intervals. A working mode is represented by the LED blinking "green" at 5 second intervals. A battery drained mode is represented when the LED is not blinking. As is apparent, the two batteries are generally used for operation of the LED.

Operation of the modules the two control modules 134 and the flow sensor 142 of FIGS. 19 through 23 may be obtained via a computer program which follows the steps outlined in the flow chart of FIG. 17. It is to be understood that the actuator of each canister 132 can be operated sequentially or independently via a computer program and the desired set up for the HVAC system. The first control module/motor of the arrangement of FIGS. 19 through 23 may be activated to operate the actuator 49 of its respective canister 132 and then the second control module/motor may be activated to operate the actuator 49 of its respective canister 132 in a sequential operation. Additionally, the first control module and the second control module may be operated independently in a manner which is apparent from the construction of the scent disperser arrangement of FIGS. 19 through 23. As described above, the scent disperser assemblies 131 are electrically interconnected with a flow sensor 142 in the same manner as shown and described with respect to the embodiment of the scent dispenser assembly 30 and sensor 28 of FIGS. 6-17. The operation of the scent disperser assembly 131 having control module 134 numbered "1" and "2", would be essentially the same as that of the embodiment of FIGS. 6-17 with the control modules 134 set to control the emitting and ceasing of spraying of scented fragrance in the HVAC system. As described, the option of operation of the dual scent disperser assemblies 131 with control modules 134 would be control module 134, numbered "1" initially inactive, activated when the canister 132 of the scent disperse assembly 131 of control module 134 numbered "2", initially active, runs out of scented fragrance, the scent disperse assembly 131, numbered "1" is activated to spray as programmed; or, as described, the scent disperser assembly 131, initially inactive, would activate after a predetermined number of sprays of scented fragrance was emitted by scent dispenser 131 having control module 134 numbered "2" and it and it deactivated and activated after a predetermined number of sprays from scent disperser assembly 131, having control module numbered "1" with it then deactivated, and the sequential shifting of the spraying continuing until either of the scent disperser assemblies 131 runs of scented fragrance.

FIG. 24 illustrates a unique construction for a canister 150 of the invention and what is referred to "Valve on a Bag". In this embodiment, the liquid L is contained within a bag 152 which is then inserted into the canister 150 and the bag 152 is surrounded by pressurized air. A valve 156 is connected to the bag 152 and is in turn connected to an actuator 154 which extends out of the canister 150. The pressurized air around bag 152 causes valve 154 to be continuously opened and therefore results in a continuous operation of actuator 156 such that a continuous spray is emitted from canister 150. In some instances, it may be desirable to meter the valve 154 and actuator 156.

FIG. 25 illustrates a canister 158 wherein the liquid L is contained in the canister 158 and a tube 160 is connected to a valve 162 and the valve 162 is operated via actuator 164. In this structure, the actuator 164 is metered, that is, the actuator 164 is pushed down and then is automatically lifted for the next operation. This is a "stop and go" spray emitting type of condition. Either type of canister 150 or 158 may be used in the scent disperser arrangement 26 of the invention disclosed herein above.

FIG. 26 illustrates a further embodiment of the invention. In this embodiment, a reservoir 166 for retaining a supply of scented liquid L is provided. The canister 150 of FIG. 24 is used wherein the actuator 154 extends into the reservoir 166. The pressure from the liquid in reservoir 166 is constantly acting on actuator 154 and a solenoid 170 operates to deliver a spray into the atmosphere. A control module 172 which may be similar to control module 134 of FIG. 19 may be used to operation solenoid 170 to emit a desired amount of sprays at a desired time interval. Solenoid 170 and control module 172 act to meter the spray from canister 150.

FIG. 27 illustrates a still further embodiment of the invention. In this embodiment, a reservoir 180 for retaining a supply of scented liquid L is provided. A sprayer disperser or aerosol 181 extends from the top of reservoir 180 for delivering a spray of fragrance. Connected to the lower portion of reservoir 180 are canisters 182, 184 and 186 which also contain a supply of scented liquid. Reservoir 180 is under a predetermined pressure $P_1$ and canisters 182, 184 and 186 are under predetermined pressures $P_2$, $P_3$ and $P_4$, respectively which preferably are less than pressure $P_1$. When the supply of scented liquid L in reservoir 180 is decreased or depleted, the canisters 182, 184 and 186 sequentially deliver scented liquid into reservoir 180 to restore the desired supply of scented liquid L in reservoir 180. It is to be understood that preferably all canisters 182, 184 and 186 are supplying liquid to the reservoir simultaneously. In this embodiment, preferably, canisters 182, 184 and 186 are of the "Valve on a Bag" type canister similar to canister 150 of FIG. 26 which allows the valve in canisters 182, 184 and 186 to remain open so that the canisters are in communication with reservoir 180.

While the present invention has been described in connection with the preferred embodiments of the various figures, it is to be understood that other similar embodiments may be used or modifications and additions may be made to the described embodiment for performing the same function of the present invention without deviating there from. Accordingly, it is intended by the appended claims to cover all such changes and modifications as come within the spirit and scope of the invention.

What is claimed is:

1. A scent dispenser arrangement for dispersing fragrances into the environment, comprising:
    a flow sensor means structured to create and emit an electrical signal for sensing the flow of air in a closed environment:
    at last one first scent disperser assembly for dispersing a scented spray and comprising a control module with a plunger assembly and a canister containing a scented fragrance with an actuator associated with the control module for actuation of the actuator for emitting a spray of scented fragrance,
    the first scent disperser assembly connected to the flow sensor means and the control module structured to receive the electrical signal from the flow sensor for operation of the canister of the first scent disperser assembly;
    a second disperser assembly electrically connected with the first disperser assembly for selective operation of the first scent disperser assembly and the second scent disperser assembly sequentially;
    wherein the control module includes means for the selectively and intermittently operating the first scent disperser assembly and the second scent disperser assembly at predetermined time intervals; and
    wherein the first scent disperser assembly and the second scent disperser assembly are electrically connected in series and wherein the control module operates in a manner that when the first scent disperser assembly runs out of liquid, the second scent disperser assembly is operated to distribute a scented spray and when the second scent disperser assembly runs out of liquid, the first scent disperser assembly is operated to distribute a scented spray in an HVAC system.

2. The scent disperser arrangement of claim 1 wherein the flow sensor comprises an anemometer having a plurality of cup elements and rotatably mounted on the flow sensor for detecting air flows and causing the cup elements to rotate to create the electrical signal which is transmitted to the module of the scent dispenser assembly.

3. The scent disperser arrangement of claim 2 further comprising an electrical connection in the form of a voltage signal connecting the flow sensor means to the control module of the scent dispenser assembly.

4. The scent disperser arrangement of claim 3 wherein the control module includes means for selectively operating the scent disperser assemblies dispersing a scented spray.

5. The scent dispenser arrangement of claim 1 wherein the control module is battery operated.

6. The scent disperser arrangement of claim 1 wherein the first scent disperser assembly further comprises an elongated tube connected to the actuator of the canister for dispersing the scented spray into a predetermined area.

7. The scent dispenser arrangement of claim 1 wherein the first scent dispenser assembly comprises a back cover, a front cover, and an elongated tube for dispersing the scented spray into a predetermined area in the HVAC system; and
    wherein the back cover and the front cover each comprises an aperture for receiving and supporting the elongated tube.

8. The scent dispenser arrangement of claim 7 wherein the HVAC system comprises ductwork and includes an air blower;
    wherein the back cover of the first scent dispenser assembly is mounted against an external wall surface of the ductwork of the HVAC system;
    wherein the flow sensor means is mounted inside the ductwork of the HVAC system remote from the air blower; and
    wherein the elongated tube extends through the aperture of the back cover and into the ductwork for dispersing the scented spray into the HVAC system.

9. The scented dispenser arrangement of claim 7 wherein the HVAC system comprises ductwork having an air blower;
    wherein the back cover of the first scent dispenser assembly is mounted against an external wall surface of the ductwork of the HVAC system;
    wherein the flow sensor means is mounted inside the ductwork of the HVAC system adjacent to the air blower; and
    wherein the elongated tube extends through the aperture of the back cover and into the ductwork for dispersing the scented spray near the air blower and into the HVAC system.

10. The scent dispenser arrangement of claim 7 wherein the HVAC system comprises ductwork and includes an air blower, an air handler system and an air filter;
    wherein the back cover of the first scent dispenser assembly is mounted against an internal wall surface of the air handler system near the air filter;
    wherein the flow sensor is mounted inside the ductwork of the HVAC system remote from the air blower and the first scent dispenser assembly; and
    wherein the elongated tube extends through the aperture in the front cover and into the air handler for dispersing the scented spray into the air filter and into the HVAC system.

11. The scent dispenser arrangement of claim 7 wherein the HVAC system comprises ductwork and includes an air blower, an air handler system and an air filter;
    wherein the first scent dispenser assembly is mounted on the floor of the HVAC system adjacent to the air filter;
    wherein the flow sensor is mounted inside the ductwork of the HVAC system adjacent to the air blower; and
    wherein the elongated tube extends through the aperture in the front cover and into the air filter for dispersing the scented spray into the air filter and into the HVAC system.

12. The scent disperser assembly of claim 1 wherein the first scent disperser assembly and the second scent disperser assembly each comprises an elongated tube for distributing a scented spray; wherein the first scent disperser assembly and the second scent disperser assembly are assembled as a unit and wherein the unit is mounted in a HVAC system and in association with a filter of the HVAC system; and wherein the elongated tube of each first scent disperser assembly and second scent disperser assembly is positioned in association with the filter of the HVAC system for operation of the scent disperser assembly and for the distribution of the scented spray into the HVAC system.

13. The scent disperser assembly of claim 1 wherein the first scent disperser assembly and the second scent disperser assembly each comprises an elongated tube for distributing scented spray; wherein the first scent disperser assembly and the second scent disperser assembly are assembled as a unit and wherein the unit is mounted in an air handler system and in association with a filter of the air handler system; and wherein the elongated tube of each scent disperser assembly is positioned in association with the filter of the air handler system for operation of the scent disperser assembly and for the distributing of the scented spray into the air handler system.

14. The scent disperser arrangement of claim 1 wherein the control module comprises a manually operable system for operating the scent disperser assembly and for delivering a scented spray at predetermined intervals.

15. The scent disperser arrangement of claim 1 wherein the control module includes a timer means for activating or deactivating the first scent disperser assembly and second scent disperser assembly for emitting or ceasing flow of scent fragrance in a cycle of predetermined minute intervals.

16. The scent disperser arrangement of claim 15 where the control module is constructed and arranged such that when an interval of timed emitted and ceased flow is interrupted due to an air flow stoppage and within the interval of ceased flow of scent fragrance the first scent disperser assembly and second scent disperser assembly are deactivated and upon resumption of a flow the first and second scent disperser assemblies are activated and the timed cycle is resumed from the beginning of the timed interval.

17. A scent dispenser arrangement for dispersing fragrances into the environment, comprising:
 a flow sensor means structured to create and emit an electrical signal for sensing the flow of air in a closed environment;
 at last one first scent disperser assembly for dispersing a scented spray and comprising a control module with a plunger assembly and a canister containing a scented fragrance with an actuator associated with the control module for actuation of the actuator for emitting a spray of scented fragrance,
 the first scent disperser assembly connected to the flow sensor means and the control module structured to receive the electrical signal from the flow sensor for operation of the canister of the scent disperser assembly;
 a second disperser assembly electrically connected with the first disperser assembly selective operation of the first scent disperser assembly and the second scent disperser assembly sequentially; and
 wherein the first scent disperser assembly and the second scent disperser assembly are electrically connected in series and wherein the control module operates in a manner that when the first scent disperser assembly is actuated to emit sprays of scented fragrance that after a predetermined number of such sprays the first scent disperser assembly is deactivated and the second scent disperser assembly is activated to spray a predetermined number of sprays of scent fragrances and further that after the number of sprays from the second spray disperser assembly is reached this first disperser assembly is activated to spray a predetermined number of sprays, and the sequential shifting of the spraying between the first and second scent disperser assemblies continues until either the first and second scent disperses assemblies runs out of scent fragrances.

* * * * *